United States Patent [19]

Summers et al.

[11] Patent Number: 5,169,784
[45] Date of Patent: Dec. 8, 1992

[54] BACULOVIRUS DUAL PROMOTER EXPRESSION VECTOR

[75] Inventors: Max D. Summers, Bryan, Tex.; Christian E. G. Oker-Blom, Turku, Finland

[73] Assignee: The Texas A & M University System, College Station, Tex.

[21] Appl. No.: 583,392

[22] Filed: Sep. 17, 1990

[51] Int. Cl.$^5$ .............................................. C12N 15/86
[52] U.S. Cl. ..................................... 435/320.1; 935/32
[58] Field of Search ........................... 435/320.1, 172.3

[56] References Cited

U.S. PATENT DOCUMENTS

| | | | |
|---|---|---|---|
| 4,745,051 | 5/1988 | Smith et al. | 435/69.51 |
| 4,879,236 | 11/1989 | Smith et al. | 435/320.1 |
| 5,004,687 | 4/1991 | Miller | 435/69.1 |

FOREIGN PATENT DOCUMENTS

| | | |
|---|---|---|
| 0260090 | 9/1987 | European Pat. Off. . |
| 0272858 | 12/1987 | European Pat. Off. . |
| 0279661 | 2/1988 | European Pat. Off. . |
| 0397485 | 11/1990 | European Pat. Off. . |
| WO89/01518 | 2/1989 | PCT Int'l Appl. . |
| WO89/07644 | 8/1989 | PCT Int'l Appl. . |
| WO91/00914 | 1/1991 | PCT Int'l Appl. . |

OTHER PUBLICATIONS

Jarvis, D. L. et al, "Use of Early Baculovirus Promoters for Continuous Expression and Efficient Processing of Foreign Gene Products in Stably Transformed Lepidopteran Cells", *Biotechnology*, vol. 8, No. 10, pp. 950-955, Oct. 1990, USA.

Hill-Perkins, M. S. & Possee, R. D., "A Baculovirus Expression Vector Derived From the Basic Protein Promoter of *Autographa californica* Nuclear Polyhedrosis Virus", *Journal of General Virology*, vol. 71, No. 4 pp. 971-976, Apr. 1990, UK.

French, T. J. & Roy, P., "Synthesis of Bluetongue Virus (BTV) Corelike Particles by Recombinant Baculovirus Expressing the Two Major Structural Core Proteins of BTV", *Journal of Virology*, vol. 64, No. 4, pp. 1530-1536, Apr. 1990, USA.

Oker-Blom and Summers, *J. Virol.* 63(3):1256-1264 (1989).

Oker-Blom et al., *Virology* 172(1):82-91 (1989).

Blissard and Rohrmann, *Virology* 170:537-555 (1989).

(List continued on next page.)

*Primary Examiner*—Richard A. Schwartz
*Assistant Examiner*—S. L. Nolan

[57] ABSTRACT

This invention relates to specifically designing and genetically engineering recombinant baculovirus for producing, in a compatible insect system, a desired protein, virus, protein hybrid, or virus hybrid. In particular aspects, this invention relates to the use of different baculovirus promoters for the ultimate purpose of constructing a recombinant baculovirus designed for the investigator's specific need. For example, the recombinant baculovirus of this invention can be designed to produce a viral pesticide.

This invention also describes the construction of a genetically engineered virus or virus hybrid (e.g. animal or human pathogen) which is not capable of replicating itself but is essentially identical to the authentic pathogen in terms of structure and antigenicity. This baculovirus is constructed such that the non-structural viral genes are truncated, mutated or both and are located 3' and directly under the control of an early baculovirus gene promoter and the structural viral genes are located 3' and directly under the control of a late baculovirus gene promoter. This genetically engineered baculovirus is therefore capable of temporal regulation and successive synthesis of non-structural and structural proteins. The truncated or mutated non-structural viral genes creates the non-replicative aspect of this invention. Since the genetically produced virus or virus hybrid is essentially identical to the authentic pathogen, the product is thereby highly antigenic and potent in terms of efficacy and efficiency. This invention enables the design and constructure of a virus particle or virus hybrid with specific antigenic properties which further allows for the safe and inexpensive production of vaccines or diagnostics.

13 Claims, 12 Drawing Sheets

OTHER PUBLICATIONS

Carbonell et al., *Journal of Virology* 56(1):153-160 (1985).
Carson, et al., *Virology*, 162:444-451 (1988).
Cochran et al., *J. Virol.*, 54:30-37 (1985).
Friesen, et al., *Molecular and Cellular Biology*, 6(5):1599-1607 (1986).
Gheysen et al., *Cell* 59:103-112 (1989).
Gonzalez, et al., *Virology* 170:160-175 (1989).
Granados and Federici (Editors), *The Biology of Baculoviruses*, vol. I, Biological Properties and Molecular Biology, Chapter 9.
Guarino and Summers, *J. Virol.* 57:563-571 (1986).
Guarino and Summers, *J. Virol.* 60(1):215-223, (1986).
Guarino, et al., *J. Virol.* 60(1):224-229 (1986).
Guarino and Summers, *J. Virol.* 61(7):209-2099 (1987).
Kajigaya, et al., *Proc. Natl. Acad. Sci. USA*, 86:7601-7605 (1989).
Karacostas et al., *Proc. Natl. Acad. Sci. USA*, 86:8964-8967 (1989).
Lanford, *Virology* 167:72-81 (1988).
Mackett et al., *Journal of Virology* 49(3):857-864 (1984).
Smith et al., *J. of Virol.* 64(6):2743-2750 (1990).
Summers, *Proceeding of American Society*, In Press (1990).
Urakawa, et al., *J. Gen. Virol.* 70:1453-1463 91989).
Webb and Summers, *Technique—A Journal of Methods in Cell and Molecular Biology*, 2(4):173-188, Aug., 1990.

FIG. 3
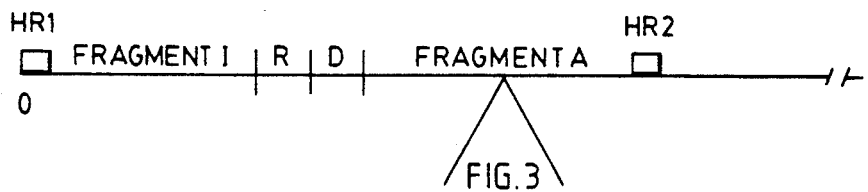
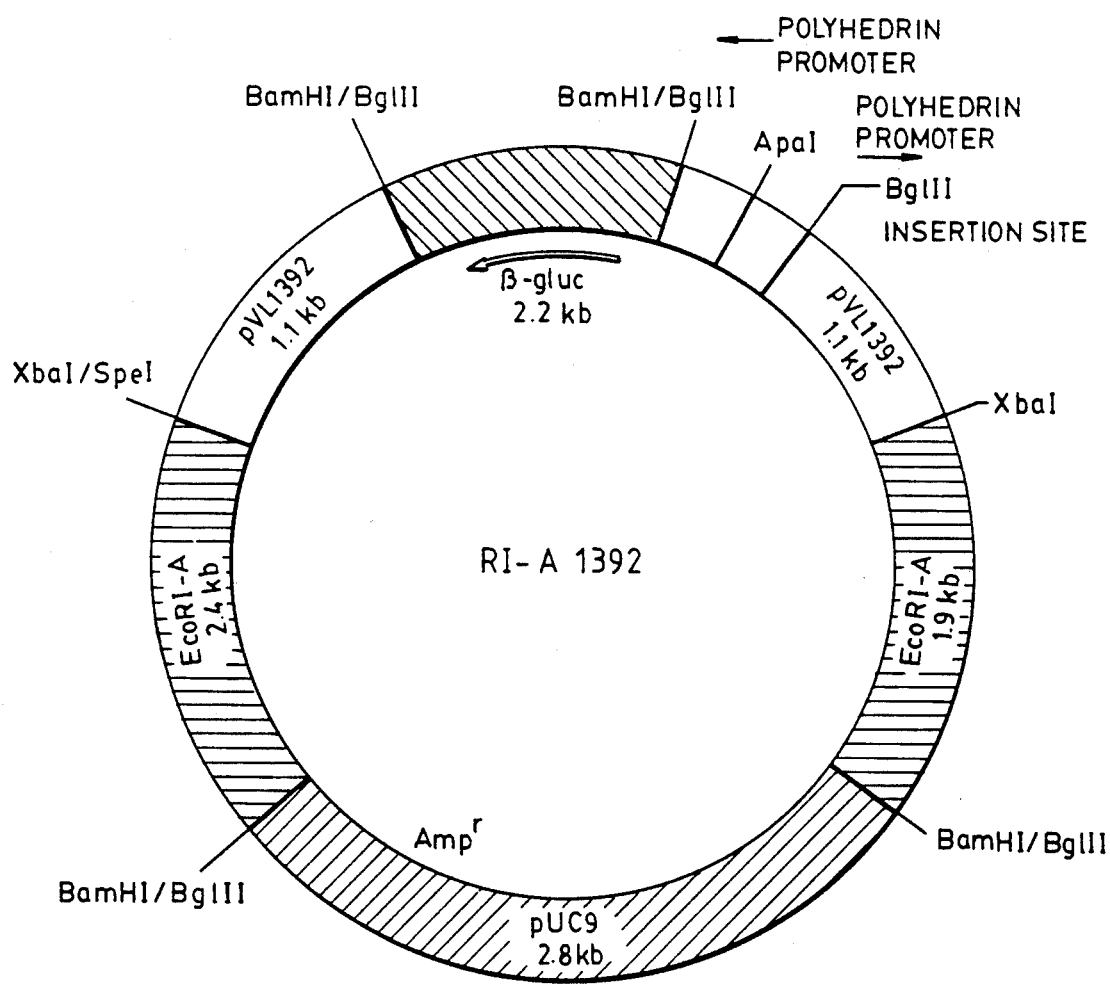

FIG.4
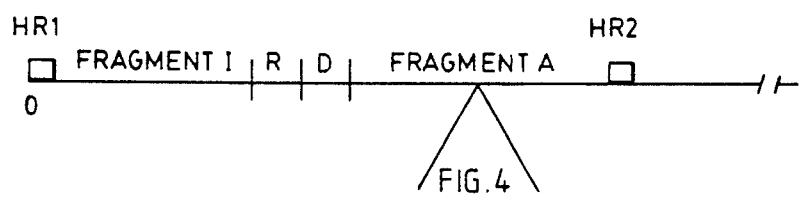
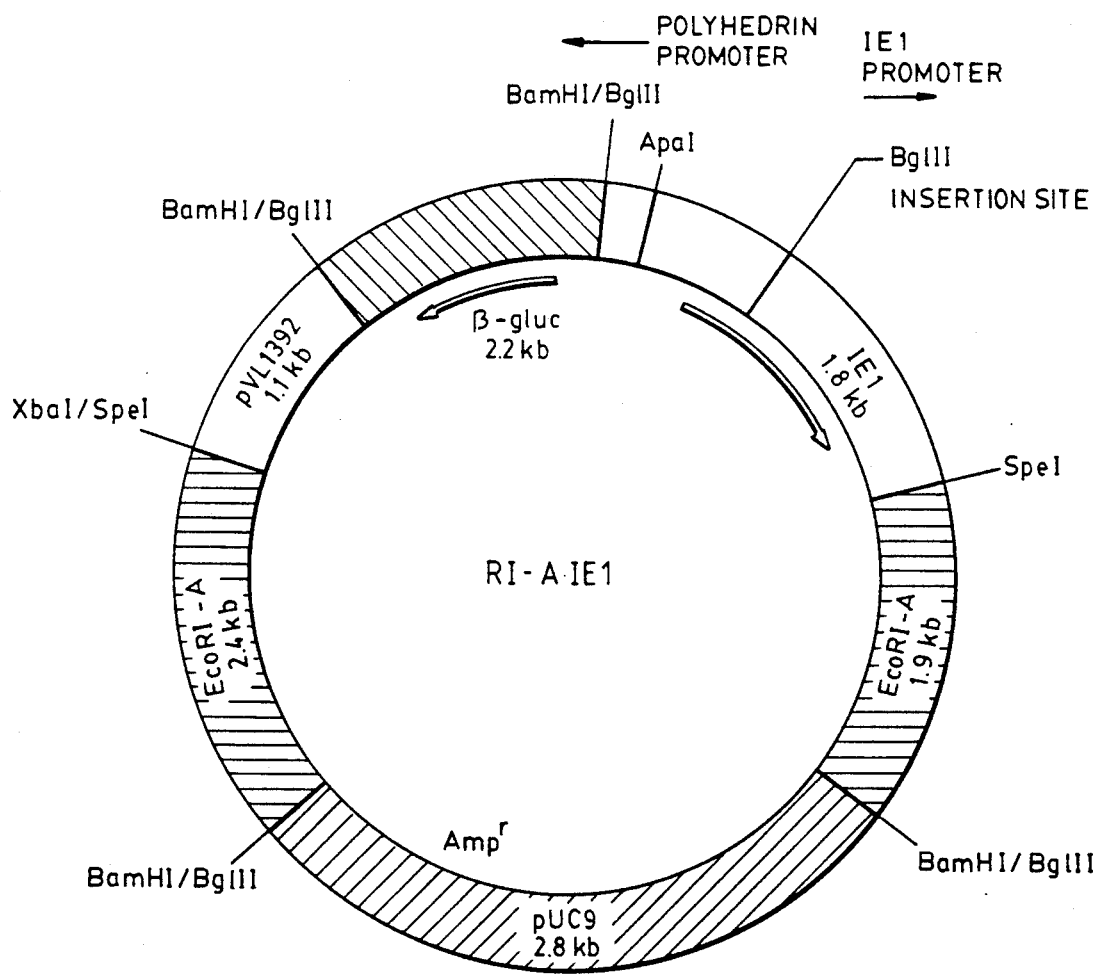

FIG. 5
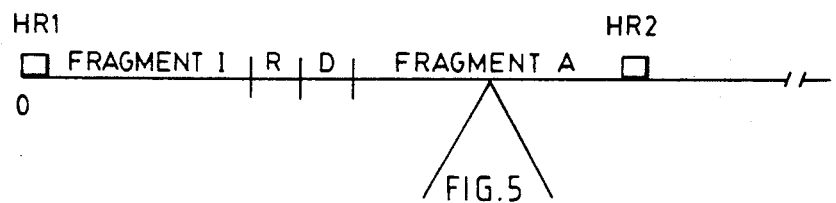
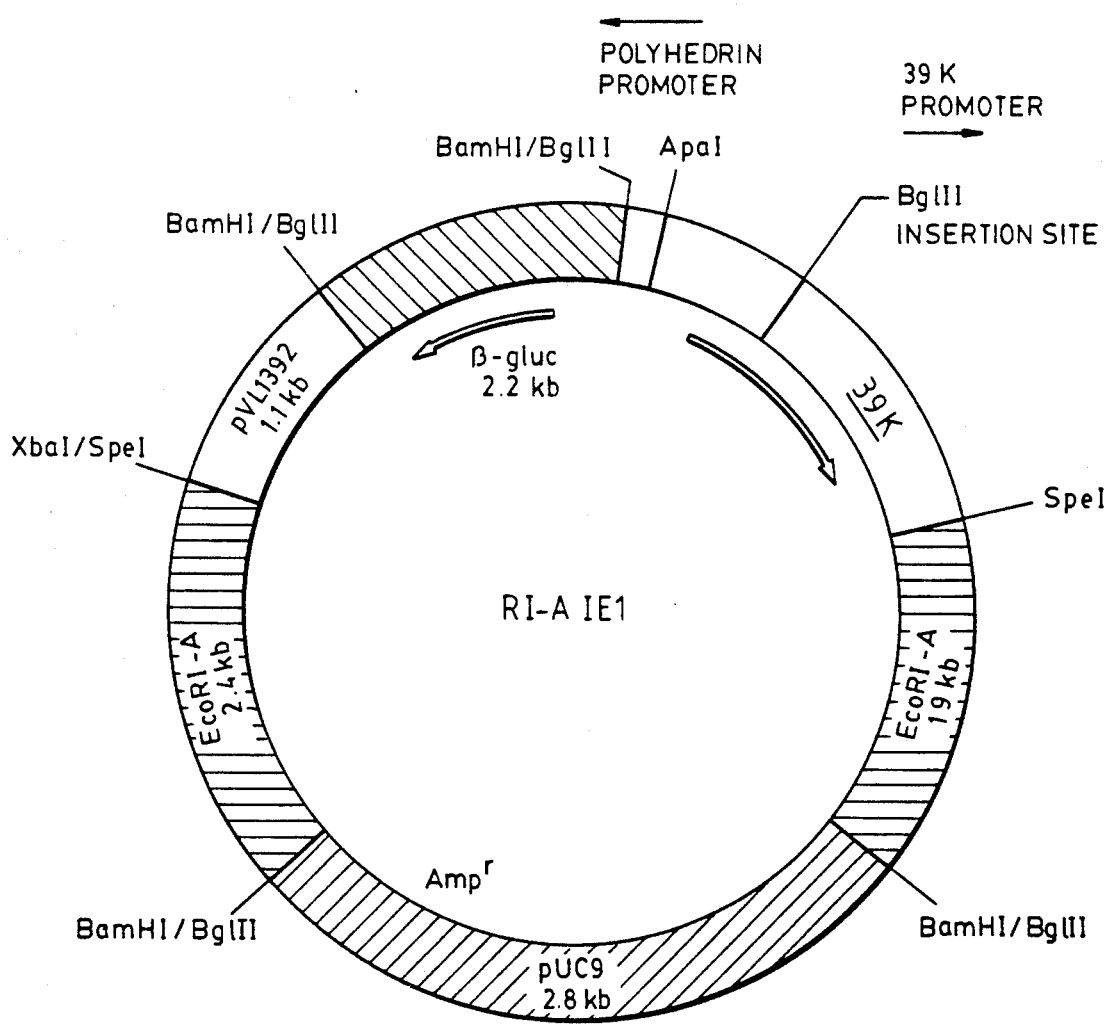

FIG.7
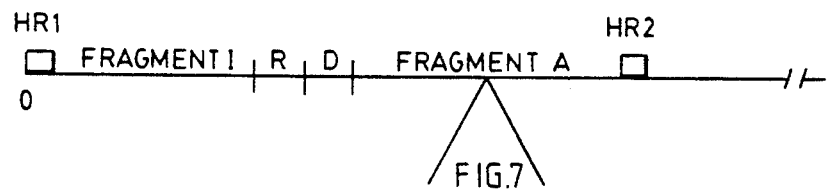
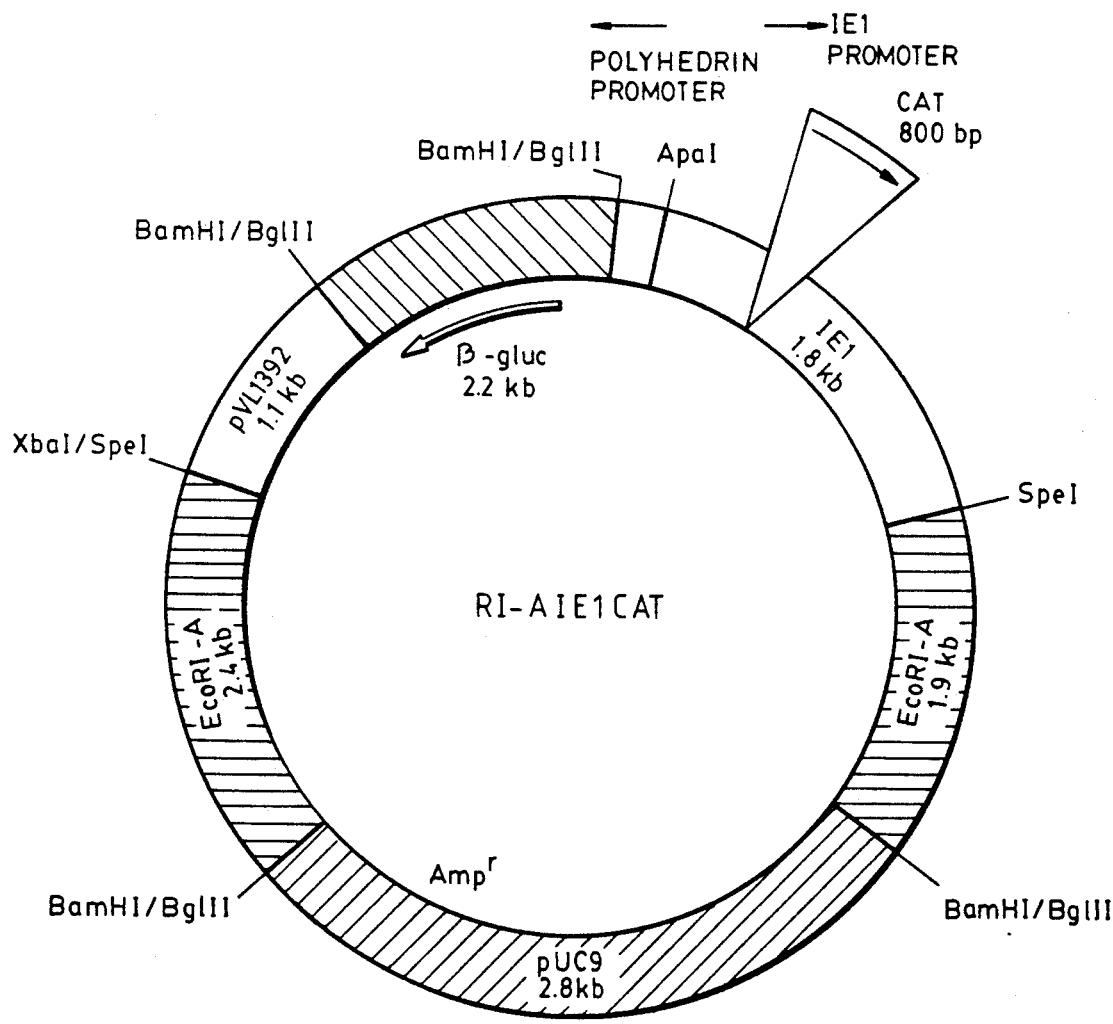

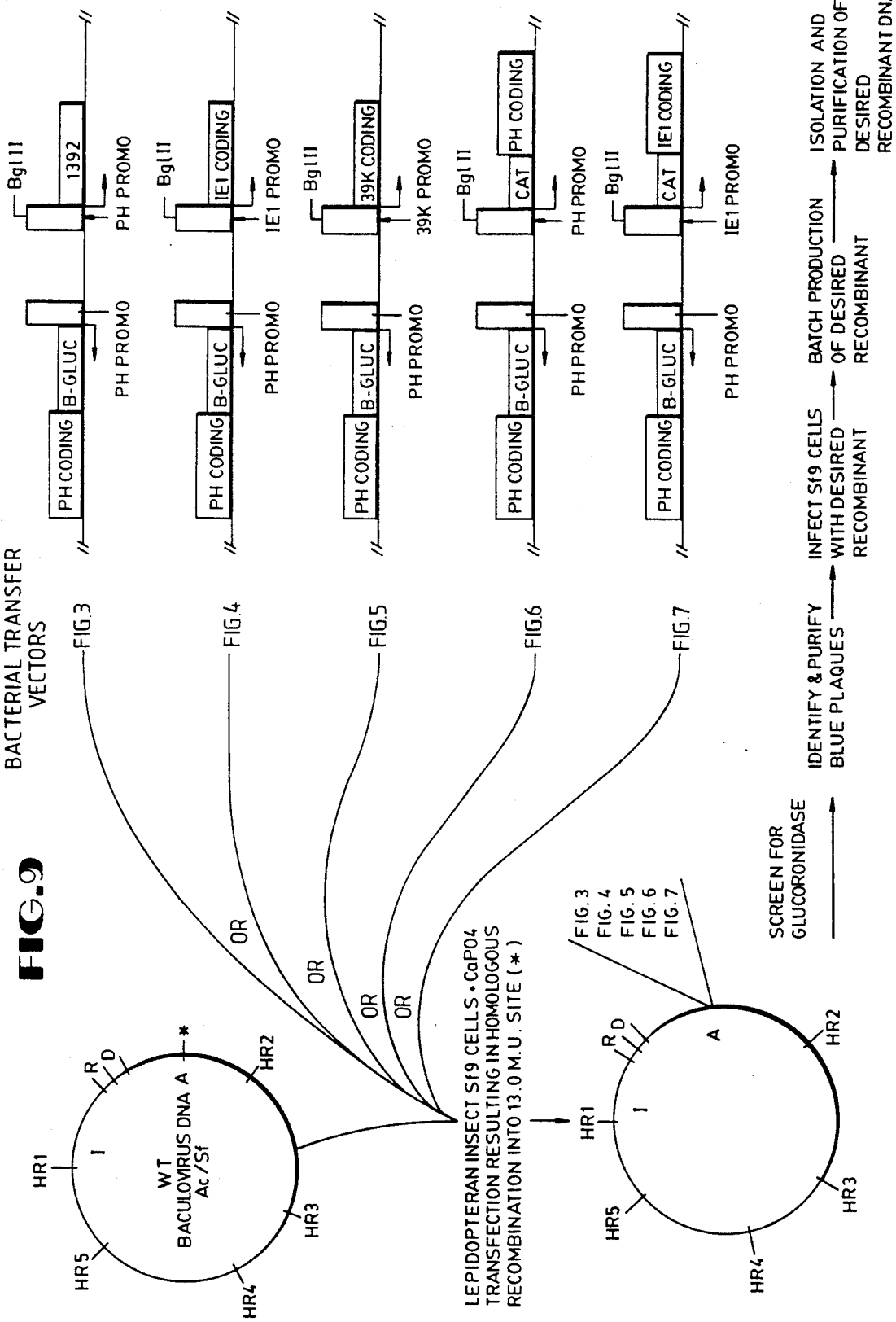

FIG.10B

LEGEND:
○ SINDBIS E1, E2
• SINDBIS CAPSID
▨ RUBELLA E1, E2

WILD-TYPE REPLICATIVE SINDBIS RNA

TRUNCATED NON-REPLICATIVE SINDBIS RNA

CAPSID
ENVELOPE

FIG.10A

LEGEND:
○ SINDBIS E1, E2
• SINDBIS CAPSID

WILD-TYPE REPLICATIVE SINDBIS RNA

TRUNCATED NON-REPLICATIVE SINDBIS RNA

CAPSID
ENVELOPE

BACULOVIRUS DUAL PROMOTER EXPRESSION VECTOR

BACKGROUND OF THE INVENTION

A. Field of the Invention

This invention relates to specifically designing and genetically engineering recombinant baculovirus for producing, in a compatible insect system, a desired protein, virus, protein hybrid, or virus hybrid. In particular aspects, this invention relates to the use of different baculovirus promoters for the ultimate purpose of constructing a recombinant baculovirus designed for the investigator's specific need.

B. Description of the Related Art

The capabilities of producing genetically engineered proteins, through the use of recombinant DNA technologies, have dramatically increased in the last decade. However, problems have accompanied these new capabilities. One of the many problems involves constructing and genetically *engineering the desired protein product*. The operative words in the last sentence are "engineering the desired protein product." All too often, when it comes to creating a construct specifically designed for the production of a desired protein or virus, comprises have to be made. It is not uncommon that many intervening and tedious steps are involved in the creation of a desired construct for the purpose of producing a desired product. It is also not uncommon to have "to settle" for the production of an almost perfect construct because of technical difficulties in designing compatible sites for insertion of desired genes.

It is the intent of this invention to detail methods and compositions for designing and creating a baculovirus construct. This construct is designed in such a manner that few if any compromises have to be made in order to create the desired product. This baculovirus construct allows for the production of virtually any protein, vaccine, therapeutic, diagnostic, viral pesticide, or virus, as well as, the creation of virtually any new combination of the above. Combinations of proteins or viruses are termed "protein hybrid" or "virus hybrid." These terms imply there are multiple sources from which the product is created or that the product itself is made up of different components.

This invention will allow the investigator to design and create desired proteins, vaccines, viruses, therapeutics, diagnostics, viral pesticides, hybrids of the above, or functional and active domains from any of the above as well. Therefore, the potential use of this vector is endless.

The success of this invention, is in part, due to the unique use of multiple baculovirus promoters (both early and late) along with homologous recombination into a non-essential region(s) of the AcMNPV genome. For optimal flexibility, this invention employs three baculovirus promoters: the natural polyhedrin promoter mapped to the Eco-RI site of Fragment I; an early baculovirus promoter and a late baculovirus promoter.

The present invention also describes the production of recombinantly generated virus or virus hybrid particles or proteins involving the novel use of an early baculovirus gene promoter to temporally drive the expression of truncated or mutated non-structural genes of a virus particle as a unit, 5' to a late baculovirus gene promoter controlling the expression of cDNA for structural genes from the same or a different virus. The recombinantly expressed virus or virus hybrid, obtained from this construct, is essentially intact, virtually identical to the authentic parent virus particle, highly antigenic yet non-replicative and is therefore exceedingly functional in terms of use as a vaccine or diagnostic reagent.

This invention allows the investigator the flexibility to design and create a baculovirus construct that produces either a desired protein, vaccine, virus, therapeutic, diagnostic, viral pesticide, hybrid of the above, or functional and active domain from any of the above as well. This invention will be accomplished efficiently and without undue experimentation.

SUMMARY OF THE INVENTION

In general and overall scope, the present invention provides a method for creating a recombinant baculovirus construct for the purpose of specifically producing a desired protein, vaccine, diagnostic, therapeutic, viral pesticide, or hybrid thereof and presenting it to the cell or organism. The vector described in this invention may also be used to produce a variety of different combinations of protein hybrids, as well as proteins or peptides that can be specifically produced at a particular time in the infection cycle to optimize the effect of that protein or peptide. Also, this invention describes designing and creating a construct for the purpose of producing functional and active domains from a specific protein, vaccine, diagnostic, therapeutic, viral pesticide, or hybrid thereof. The exact regions that encompass the functional and active domain will vary from protein to protein, from vaccine to vaccine, from diagnostic to diagnostic, etc.

More particularly, the present invention describes the use of multiple baculovirus promoters representative of different classes of promoters, as well as homologous recombination to a non-essential region of the AcMNPV genome, to produce the desired protein, vaccine, diagnostic, therapeutic, viral pesticide, or hybrid thereof.

This invention also pertains to designing and creating a desired recombinant baculovirus construct for the specific purpose of producing a desired protein, vaccine, diagnostic, therapeutic, viral pesticide, or hybrid thereof. Further in accordance with this invention, hybrids of either a desired protein, vaccine, diagnostic, therapeutic, or viral pesticide are defined and designed.

In addition to the above, the recombinant DNA vector includes a DNA region comprising a cDNA sequence coding for a desired protein. Sequences coding for a variety of different genes are known to those skilled in the art and are commercially available from American Type Culture Collection (ATCC, Rockville, Md.). For example, the following is a brief list representing the range of cloned genes or probes available from ATCC: epidermal growth factor receptor, beta-glucuronidase, Y-mos M1 Maloney sarcoma virus, tissue-type plasminogen activator, arginosuccinate synthetase, insulin (A and B chain), prolactin, interleukin 1 and 2, colony stimulating factor, tumor necrosis factor, beta-hemoglobulin, interferon, leutinizing hormone, beta-hexosaminadase, coagulation factor VIIIC, transferrin, esterase D, adenosine deaminase, etc. This cDNA sequence is further comprised of nucleotide sequences coding for a desired protein having a deleted 5' untranslated region, and a deleted or mutated translational initiation site. In terms of this invention, amino acid and nucleotide numbers will be used interchangeably with the appropriate conversion factor employed.

For enhanced expression and production of the desired protein, this recombinant DNA vector, in addition to the above stated components, includes a DNA region comprising unique signals for the initiation of transcription and translation positioned 5'.

In terms of infecting or transfecting yeast or eukaryotic cells with a recombinant DNA vector, these techniques are standard and known to those skilled in the art of recombinant DNA technology. In terms of transfecting cells with the recombinant DNA vector described above, this invention could also be applied for the production of stable cell lines which are, by definition, continuously producing the specific chimera protein. The production of cell lines with stably integrated recombinant DNA vectors has been described extensively in the literature, practiced for years, and is therefore known to those skilled in the art.

It should be noted that genes may be structurally similar but that a variety of regulatory processes, which occur at the transcriptional and translational levels and function in a manner consistent with the biology of the organism or the cell, makes it impossible to predict the exact process by which the gene will be expressed and/or regulated.

The present invention also provides a method for producing a highly antigenic non-replicative virus or virus hybrid, to be used as a vaccine, a protein producing system, or a diagnostic reagent, by employing the baculovirus expression vector system (BEVS). The production of a highly antigenic non-replicative virus or virus hybrid particle involves the construction of, for example, a recombinant baculovirus expression vector containing two or three promoters genetically engineered to include foreign genes (e.g. non-structural and structural) inserted under the transcriptional regulation of both early and late baculovirus gene promoters. Thus, truncated or mutated non-structural genes will be expressed early to provide genomic, non-replicative RNA (or DNA) followed by late expression of structural genes. This strategy will ensure the availability of genomic material, which is needed for proper assembly of the virus particle of choice. Below, Sindbis virus and Rubella virus (Alphavirus) or combinations thereof will serve as examples for the clarification of this concept. It should be emphasized that the invention can be adapted or applied to a large variety of viral pathogens, insect pesticides, protein production systems and that the examples described below serve only as models. The insect pesticides can be designed to produce a desired protein, peptide, as well as an mRNA or DNA fragment which could result in insecticidal affects.

More particularly, the present invention describes the production of recombinantly generated virus or virus hybrid particles or proteins involving the novel use of an early baculovirus gene promoter to temporally drive the expression of truncated or mutated non-structural genes of a virus particle as a unit, 5' to a late baculovirus gene promoter controlling the expression of cDNA for structural genes from the same or a different virus. The recombinantly expressed virus or virus hybrid, obtained from this construct, is essentially intact, virtually identical to the authentic parent virus particle, highly antigenic yet non-replicative and is therefore exceedingly functional in terms of use as a vaccine or diagnostic reagent.

The recombinant baculovirus produced from this invention is controlled through transcriptional regulation of both early and late baculovirus gene promoters to temporally and successively synthesize both non-structural and structural proteins. Due to the temporal regulation and subsequent expression of genes under the control of different baculovirus promoters, the truncated or mutated non-structural genes are expressed first (because of control by an early baculovirus gene promoter) and the structural genes are subsequently expressed thereby allowing for the accurate assembly of a viral or viral hybrid particle. Thus, the different portions of the pathogen (non-structural versus structural) will be transcriptionally regulated by both early and late baculovirus gene promoters to produce e.g. Sindbis virus particles.

In terms of this invention, "recombinant baculovirus expression vector" or "recombinant baculovirus" refer to vectors or baculoviruses which have the ability to genetically produce both non-structural and structural proteins derived from either the same or different viral sources. It is the final vector or baculovirus described in the production scheme that contains the genetic material to produce different recombinant proteins (non-structural and structural).

Additionally, in terms of this invention, "bacterial transfer vector" shall be defined as the bacterial plasmid vector optimally containing the following: viral flanking sequences essential for optimal homologous recombination to occur, bacterial plasmid sequences, either an early or late baculovirus gene promoter, cDNA and genomic DNA encoding for both non-structural or structural viral genes and a multiple cloning site adjacent to the specific promoter. Genomic DNA is defined as DNA isolated from the chromosome of an organism or virus. The bacterial plasmid sequences may be derived from any one of the many different vectors that are commercially available and known to those skilled in the art of recombinant DNA technology. For the purpose of this invention, pUC8 is used as a matter of preference, however, other vectors would be equally effective.

These bacterial plasmid transfer vectors are utilized in cotransfection experiments, and through the process of homologous recombination or by any process in which the vectors may serve as a vehicle to deliver the desired gene or gene product, allows for the insertion or integration of the gene of interest into the baculovirus. The process of homologous recombination is standard and known to those skilled in the art. The detailed procedures are available in many different protocol texts.

In addition to the temporal transcriptional regulation, this invention also enables the design, construction and assembly of a non-replicative virus particle or virus hybrid, which is highly antigenic and functionally identical to the authentic parent virus particle. Due to the truncation or mutation of the RNA encoding for the non-structural viral genes, this novel and genetically engineered virus is therefore not capable of replicating itself, and yet, it is structurally, and antigenically, essentially identical to the authentic pathogen. The truncation or mutation must not, however, alter the genomic RNA in such a way that the genomic sequences needed for encapsidation are deleted.

An advantage and novel aspect of this invention is the freedom to design a recombinant baculovirus expression vector that can be used for the expression and production of a completely different non-replicative virus hybrid of choice. The basic concept is to genetically engineer different portions of genomic DNAs or cDNAs from different pathogens (human, animal or plant) for which a vaccine or diagnostic is needed. The non-structural gene will be derived from one viral source while the structural gene will be derived from a different viral source. This freedom in designing virtually any combination of viruses should allow for the production of highly antigenic, "special-order", potent and very specific vaccines or diagnostics.

In one embodiment of this invention, an example of a double recombinant virus hybrid is described which combines non-structural genes from Sindbis virus and structural genes from Rubella virus. The virus hybrid produced from this example is one of many different potential combinations involving an animal and a human pathogen. From this point of view, the combinations are therefore endless.

Another advantage of this invention is that it enables the production of "natural," highly potent, non-infectious antigens or combinations of assembled antigens. Generally, an intact virus particle is a better antigen and or immunogen than is a single purified protein or derivatives thereof. The product from this method for producing a vaccine or diagnostic of choice, is more efficient, safe, inexpensive and effective as compared to the more traditional procedures (i.e. attenuating the virus or virus subunit production). Thus, this invention represents an important potential improvement in the area of vaccine production compared to the available traditional vaccine production protocols.

The genetically engineered virus produced from this invention may be derived from a human, animal or plant pathogen or combinations thereof. The pathogen or viral source for the production of a recombinant baculovirus expression vector can be from the family of arboviruses which includes, but is not limited to: Sindbis virus, bluetongue virus, rabies virus, yellow fever virus, St. Louis encephalitis virus, Colorado tick fever virus or dengue fever virus.

The viral source for the production of a virus or virus hybrid may also be derived from, but is not limited to include: poliovirus, influenza virus, hepatitis B virus, human immunodeficiency virus, polyoma virus, Punta Toro phlebovirus, Simian rotavirus or Simian virus.

In accordance with the present invention, the recombinant baculovirus expression vector which will be used to produce a foreign virus or virus hybrid will minimally include a DNA region comprising a transcriptional regulator, a cDNA region or genomic DNA encoding a truncated or mutated non-structural gene for a desired viral particle, a DNA region comprising a different transcriptional regulator and a cDNA or genomic DNA region encoding a structural gene for a desired viral particle. These components are properly spaced and only use one open reading frame.

In terms of this invention, "transcriptional regulator" is defined as a promoter which controls and drives the expression of a gene located downstream (3') the promoter itself.

In accordance with the present invention, "transcriptional regulator" shall be further defined as a promoter derived from either an early or late baculovirus gene. For the purpose of this invention, an "early" baculovirus gene promoter is meant to include promoters derived from intermediate- early as well as delayed-early baculovirus genes. Examples of intermediate- and delayed-early baculovirus genes are IE1, IE0 and IEN, respectively. The promoters derived from these two early baculovirus genes have previously been shown to be strong promoters with respect to driving the expression of the specific genes located 3' to the promoter itself. Other promoters would probably be effective, however, the inventors prefer to employ the promoters derived from IE1, IE0 or IEN early baculovirus genes.

Additionally, for the purpose of this invention, promoters derived from "late" baculovirus genes include those promoters derived from the polyhedrin or p10 genes. Other promoters would probably be effective, however, the inventors prefer to employ the promoters derived from polyhedrin or p10 late baculovirus genes.

Further in accordance with this invention, the recombinant baculovirus expression vectors as well as the promoters employed to drive the expression of the viral genes, may be derived from *Autographa californica* nuclear polyhedrosis virus, *Trichoplusia ni* nuclear polyhedrosis virus, *Rachiplusia ou* nuclear polyhedrosis virus or *Galleria mellonella* nuclear polyhedrosis virus, *Heliothis zea* nuclear polyhedrosis virus, *Mamestra brassica* nuclear polyhedrosis virus, *Spodoptera exigua* nuclear polyhedrosis virus, *Spodoptera frugiperda* nuclear polyhedrosis virus, *Orgyia pseudosugata* nuclear polyhedrosis virus, *Anisota senatoria* nuclear polyhedrosis virus, or any one of the more than 500 additional baculovirus species. Although the invention described herein employs the use of baculoviruses and promoters from *Autographa californica* nuclear polyhedrosis virus as a matter of preference, any of the above mentioned polyhedrosis viruses would be as effective.

In terms of this invention, "directionally positioned", "in an appropriate open reading frame", "from 5' to 3' with appropriate spacing" and "adjacent to" are interchangeable terms referring to the positional placement of certain components in the baculovirus expression vector or the bacterial transfer vector to maintain the necessary requirements (positioning and open reading frame) for efficient and accurate transcription.

The various techniques which have been successfully applied to the cloning and expression of many heterologous genes in a variety of host systems, employing many different promoters and expression vectors, are known to those skilled in the art of recombinant DNA technology and could be applied to the embodiments described herein. Appropriate positional spacing between the numerous recombinant DNA vector components (directionally positioned 5' to 3') would be determined for each specific recombinant baculovirus vector or bacterial transfer vector and are included to further optimize the expression and production of the desired virus or virus hybrid.

In terms of this invention, a foreign virus or virus hybrid is defined as any viral particle produced in the baculovirus expression system which normally would not be made in that system.

For the purpose of this invention, virus hybrid or viral hybrid particles will be used interchangeably and will be defined as any particles produced in the recombinant baculovirus expression vector system, whereby the non-structural and structural genes are derived from two different viral sources (e.g. non-structural genes derived from Sindbis virus and structural genes derived from Rubella virus).

For the purpose of this invention, non-structural viral genes shall refer to those viral genes that encode for essential viral proteins needed for authentic viral replication and assembly. Structural viral genes will refer to those genes that encode for capsid, core and/or envelope proteins (antigenic or immunogenic epitopes). Non-structural may as well refer to a limited nucleic acid sequence needed for the formation or assembly of the capsid or core structure.

In addition to the above mentioned features, for added ease in handling and manipulating, this recombinant baculovirus expression vector could include a DNA region comprising a multiple cloning cassette sequence, appropriately spaced and in frame, between the transcriptional regulator and the non-structural viral genes or the structural viral genes. Multiple cloning cassette sequence cartridges are commercially available from several different companies (Promega, New England Biolabs, etc). A typical cassette sequence cartridge would include restriction sites for 8–11 different enzymes (i.e. Eco R1, Sac1, Sma 1, Ava 1, Bam H1, Xba 1, Hinc II, Acc 1, Sal 1, Pst 1, Hind III, etc.). The availability of these cassette cartridges are known to those skilled in the art.

Further in accordance with this invention, the recombinant baculovirus expression vector infects a suitable cell line in order to produce a functional virus or virus hybrid. Lepidopteran insect cells derived from e.g. *Spodoptera frugiperda, Heliothis virescens, Heliothis zea, Mamestra brassicae, Estigmene acrea* or *Trichoplusia ni* are used. Although cell lines derived from the above mentioned species would be effective, cell lines derived from *Spodoptera frugiperda* are preferred. Sf9 cells or Sf9 IE1-helper cells are two commonly available *Spodoptera frugiperda* cell lines which are routinely utilized.

Thus, optimal production of a specific virus or virus hybrid could potentially be enhanced if the recombinant baculovirus expression vector was engineered to include an IE1 or IEN early baculovirus gene promoter positioned 5' to cDNA and genomic DNA encoding truncated or mutated non-structural genes for a specific virus, both of which are located adjacent to a polyhedrin or p10 late baculovirus gene promoter positioned next to cDNA encoding structural genes for a specific virus. The above transfer vectors and appropriate baculoviral DNA would then be cotransfected into Sf9 or Sf9 IE1-helper Lepidopteran insect cells. This optimal expression vector, as described above, would also include the appropriate transcriptional start and stop signals as well as multiple cloning sites located 3' to the promoters for ease in inserting the cDNA encoding for the desired viral genes.

Once cotransfection and homologous recombination occurs in the above mentioned experiments, baculoviral DNA containing the recombinant will be selected by visual selection of white occlusion negative plaques. Plaque selection and purification are known procedures familiar to those skilled in this art.

The non-replicative recombinant will then be purified from the cells or culture medium by techniques known to those skilled in the art and the virus or virus hybrid is ready for further use as a vaccine or as a diagnostic reagent.

The viral or viral hybrid products obtained from this invention are inexpensive to produce, safe to use, highly antigenic and potent, and functionally very similar to the authentic parent virus.

Figure 1A:
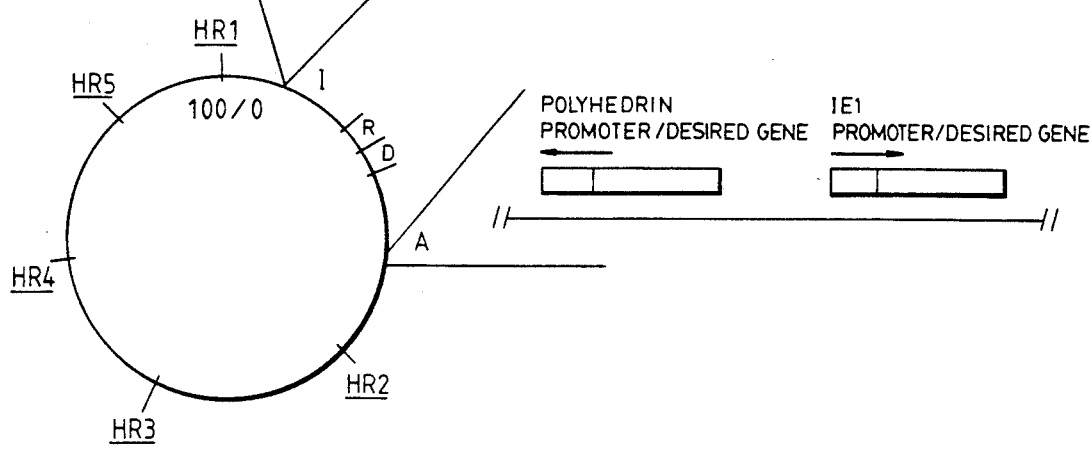
FIG 1

Model Baculovirus Expression Vector Containing Three Baculovirus Promoters for Recombinant Protein, Virus, Protein Hybrid or Virus Hybrid Production The construction of a model expression vector which would be employed for recombinant protein, virus, protein hybrid or virus hybrid production is diagramed.

FIG. 1A

100/0: arbitrary designation of map units. Zero map units start to the right of the "HR1" and 100 map units ends to the left of "HR1."

HR1–HR5: enhancer sequences numbered numerically for convenience. When a combination of immediate-early genes and a delayed-early gene promoter region is employed, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

I.R.D.A: fragments assigned letters according to size; "Fragment A" being the largest.

Polyhedrin Promoter/desired gene: designates the baculovirus polyhedrin promoter with a desired gene of choice inserted 3' to the polyhedrin promoter. 3' is defined as the region located downstream of the compared component.

Late Promoter/desired gene: designates a baculovirus late promoter with a desired gene of choice inserted 3' to the polyhedrin promoter. 3' is defined as the region located downstream of the compared component.

Early Promoter/desired gene: designates a baculovirus early promoter with a desired gene of choice inserted 3' to the polyhedrin promoter. 3' is defined as the region located downstream of the compared component.

Arrows → or ←: designates the direction that a transcriptional regulator controls and drives the expression of a gene located downstream (3') to the promoter itself.

Ninety Degree Wedge Angle: designates the area that is enlarged for viewing.

FIG. 1B

This figure demonstrates one of the many different combinations that may be employed in this model baculovirus expression vector. This model expression vector contains three baculovirus promoters adjacent to desired genes: the first polyhedrin promoter appears in its natural site within Eco-RI Fragment I. The second promoter is a polyhedrin promoter, adjacent and 5' to a desired gene, inserted through homologous recombination into a non-essential region of the baculovirus genome. The arrow indicates the direction the promoter expresses the adjacent DNA. Also, inserted through homologous recombination into this non-essential region of the genome, is a third promoter. This third promoter is an early or immediate early baculovirus promoter, for example IE1 or IEN. In this example, the immediate early baculovirus promoter, IE1, is adjacent to a desired gene and the promoter directs the expression of the desired gene (indicated by the arrow). The two promoters in the non-essential region of the genome are expressed in opposite directions. A non-essential region of the baculovirus genome is defined as a place where insertion or modification of natural viral DNA sequence or gene structure has no effect on infectivity of the modified virus in cell culture or the insect.

FIG. 2A

Map and Gene Products Indicated for AcMNPV

Figure 2A:
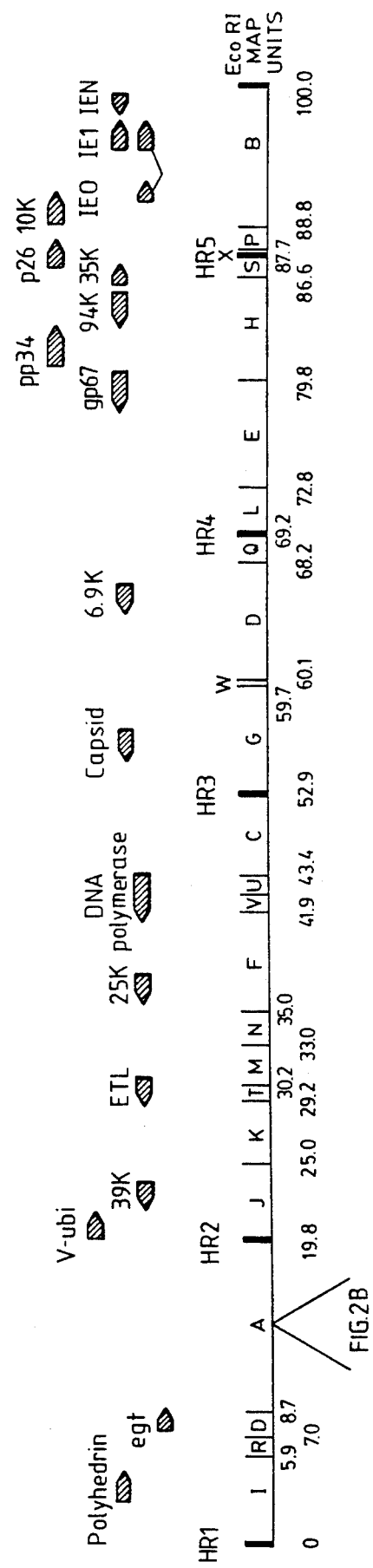

FIG. 2A schematically represents a map of AcMNPV. The gene products are indicated above the horizontal line.

Gene Products: 15 different gene products are indicated by the bold, filled in arrow heads. Examples of gene products are: Polyhedrin, egt, V-ubi, 39K, ETL, 25K, DNA polymerase, capsid, etc.

Eco-RI Map Units 100/0: arbitrary designation of map units, for the fragments generated from the restriction enzyme Eco-RI, are indicated by small numbers below the solid horizontal line. Zero map units start at the right of "HR1" and 100 map units ends at the left of "HR1."

HR1, HR2, HR3, HR4, and HR5: enhancer sequences numbered numerically for convenience. When a combination of immediate-early genes and a delayed-early gene promoter region is employed, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

I, R, D, A, J, K, T, M, N, F, V, U, C, G, W, D, O, L, E, H, S, X, P, and B: fragments generated by the restriction enzyme Eco-RI are assigned letters according to size; "Fragment A" is the largest, "B" is the next largest, "C" is the next largest, etc.

Figure 2B:
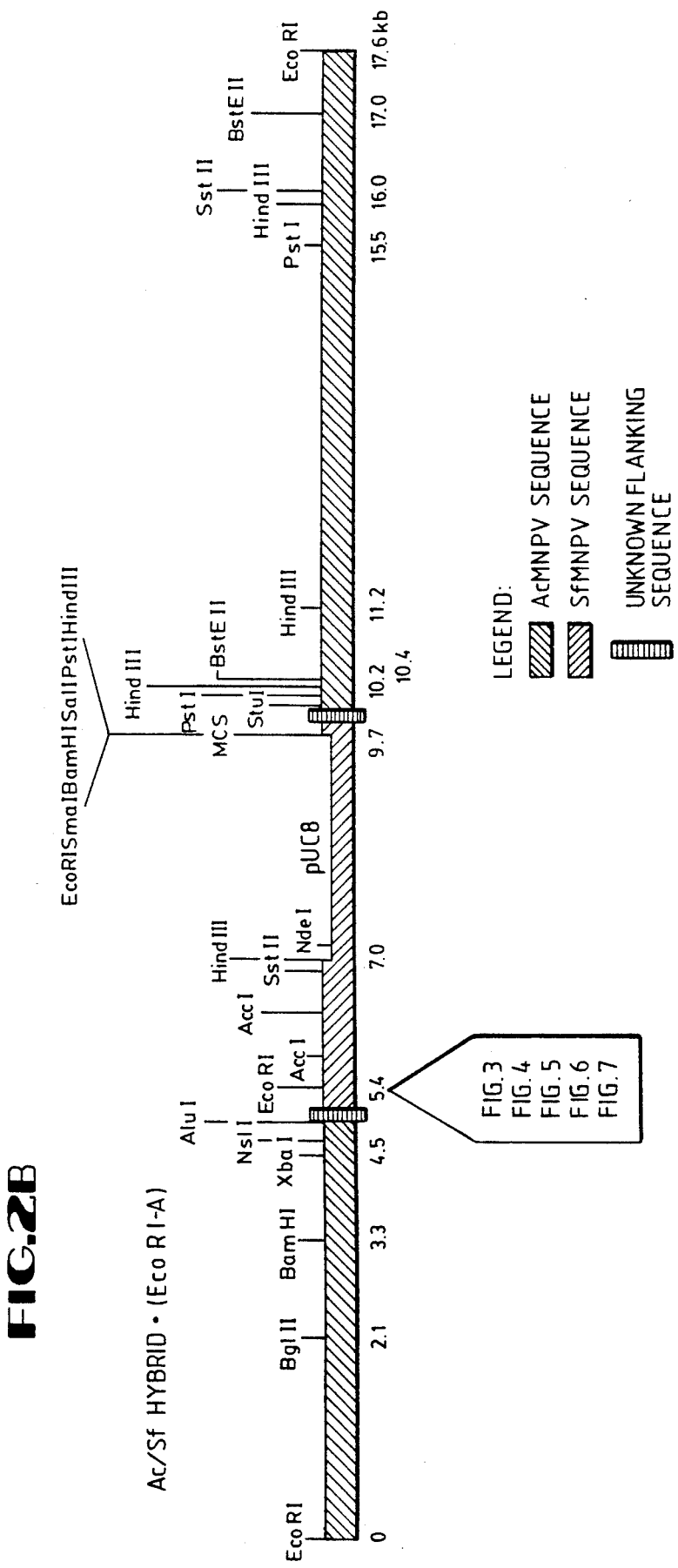

FIG. 2B Wedge: indicates the area where pSfHindIII-L will recombine into the AcMNPV [.d10A] polyhedrin deletion mutant.

FIG. 2B

Recombination of pSfHindIII-L into the AcMNPV.d10A Polyhedrin Deletion Mutant

Recombination of pSfHindIII-L into the AcMNPV.d10A polyhedrin deletion mutant. Only AcMNPV.EcoR1-A and the physical alterations of the fragment are shown. The majority of Pst1-O was deleted and a 3.7 kb fragment from pSfHindIII-L is inserted in its place. Horizontal lines represent transcripts and their orientation. Dashed lines indicate possible termination sites. Genomic map units (m.u.) are shown at specific sites beneath correlating fragment dimensions. The wedged area is magnified in subsequent figures to present more detail.

FIG. 3

Construction of Transfer Vector RIA-1392

RIA-1392 is designed to contain a unique Bgl II site for the insertion of foreign genes under the control of a polyhedrin promoter. Foreign genes are inserted at +35 in relation to the polyhedrin translation start ATG. RIA-1392 also contains the B-glucoronidase gene under the control of a polyhedrin promoter for use as a selectable marker. This transfer vector contains 1.9 and 2.4 kb of EcoR1-A viral flanking sequences.

FIG. 4

Construction of Transfer Vector RIA-IE1

RIA-IE1 contains a unique Bgl II site for the insertion of foreign genes under the control of a early baculovirus IE1 promoter. Foreign genes are inserted at −39 in relation to the IEI translation start ATG. RIA-IE1 also contains the B-glucoronidase gene under the control of a polyhedrin promoter for use as a selectable marker. This transfer vector contains 1.9 and 2.4 kb of EcoRI-A viral flanking sequences.

FIG. 5

Construction of Transfer Vector RIA-39K

RIA-39K contains a unique Bgl II site for the insertion of foreign genes under the control of a baculovirus 39K promoter. Foreign genes are inserted at −80 in relation to the 39K translation start codon. RIA-39K also contains the B-glucoronidase gene under the control of a polyhedrin promoter for use as a selectable marker. This transfer vector contains 1.9 and 2.4 kb of EcoRI-A viral flanking sequences.

FIG. 6

Construction of Vector RIA-1392-CAT

Construct RIA-1392-CAT contains the chloramphenicol acetyl transferase gene (CAT) under the control of one polyhedrin promoter and B-glucoronidase gene under the control of another polyhedrin promoter for use as a selectable marker. This transfer vector contains 1.9 and 2.4 kb of EcoRI-A viral flanking sequences.

FIG. 7

Construction of Vector RIA-IE1-CAT

Construct RIA-IE1-CAT contains the chloramphenicol acetyl transferase gene (CAT) under the control of IE1 promoter and the B-glucoronidase gene under the control of a polyhedrin promoter for use as a selectable marker. This transfer vector contains 1.9 and 2.4 kb of EcoRI-A viral flanking sequences.

FIG. 8

Linear Representation of Vector RIA-IE1-CAT

Linear representation of vector RIA-IE1-CAT which contains the chloramphenicol acetyl transferase gene (CAT) under the control of IE1 promoter and the B-glucoronidase gene under the control of a polyhedrin promoter for use as a selectable marker. This transfer vector contains 1.9 and 2.4 kb of EcoRI-A viral flanking sequences.

FIG. 9

Homologous Recombination of a Desired Recombinant Baculovirus Transfer Vector into the 13.0 Map Unit Nonessential Region of Wild Type Baculovirus FIG. 9 diagrams the homologous recombination of a desired recombinant baculovirus transfer vector into the 13.0 map unit nonessential region of wild type baculovirus. The construction of different bacterial transfer vectors are described in the examples above. The polyhedrin-beta-glucoronidase containing recombinant baculovirus produces blue plaques. This selectable marker allows for easy identification of desired recombinants (via observing blue plaques). Once Sf9 cells are infected with the desired recombinant, this desired recombinant may further be propagated, isolated, and purified.

FIG. 10 (parts A and B)

Genetic Engineering of a Non-Replicative Virus or Virus Hybrid Using the Baculovirus as a Tool FIG. 10A presents a schematic representation of constructing a non-replicative virus by truncating the RNA which encodes for the non-structural proteins for that virus. The source of the viral genome structural and non-structural genes are the same. Sindbis virus is used as an example only.

FIG. 10B HYBRID is a schematic representation of constructing a non-replicating virus hybrid. The non-replicative aspect results from truncating the RNA encoding the non-structural genes; the virus hybrid is constructed by producing non-structural genes from Virus A and structural genes from Virus B. Truncated Sindbis non-structural genes and structural Rubella genes are used as examples only.

FIG. 11

Figure 11:
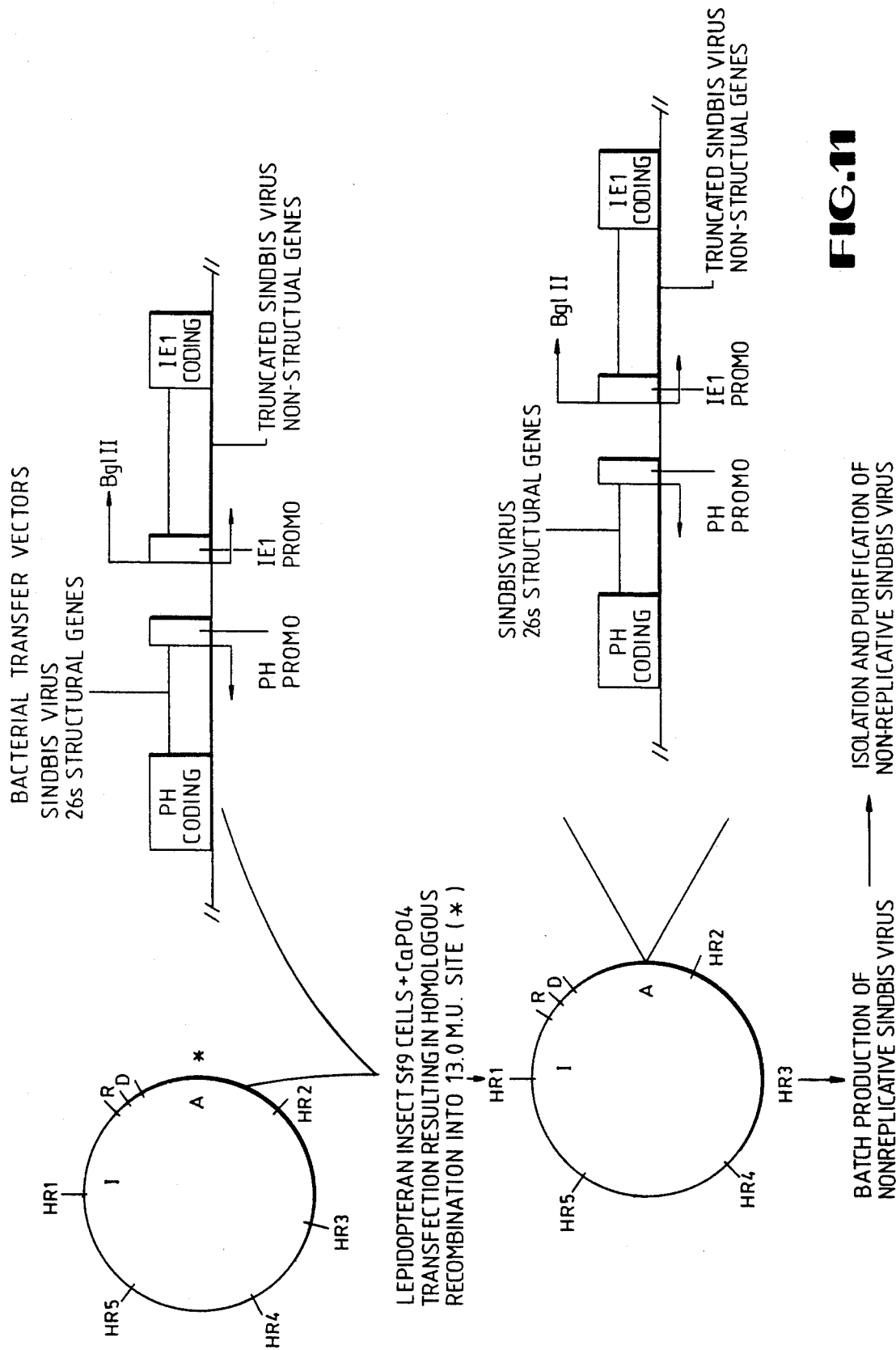

Homologous Recombination of a Non-Replicative Sindbis Virus into the 13.0 Map Unit Nonessential Region of Wild Type Baculovirus FIG. 11 diagrams the homologous recombination of a non-replicative Sindbis virus into the 13.0 map unit nonessential region of wild type baculovirus. Truncated genomic non-structural Sindbis virus cDNA and 26S are used as an example only. This is achieved by cloning a mutant (truncated) non-structural Sindbis virus gene under the control of an IE1 early baculovirus promoter. The completed bacterial transfer vector is generated in a two-step fashion. First the truncated Sindbis virus non-structural gene is inserted under the control of an early baculovirus promoter (for example, IE1). The next step involves inserting genes encoding intact structural Sindbis viral 26S proteins under the transcriptional regulation of a late baculovirus gene promoter (for example, polyhedrin). This insertion is performed on the recombinant baculovirus which already contains non-structural genes under the regulation of an early baculovirus gene promoter.

DETAILED DESCRIPTION OF THE PREFERRED EMBODIMENTS

Autographa Californica Nuclear Polyhedrosis Virus (AcMNPV)

*Autographa californica* nuclear polyhedrosis virus (AcMNPV), the prototype virus of the family Baculoviridae, has a wide host range and infects more than 30 species of Lepidopteran insects. During AcMNPV infection, two forms of viral progeny are produced: extracellular virus particles (ECV) and occluded virus particles (OV). The latter are embedded in proteinaceous viral occlusions, called polyhedra. A polyhedrin protein, with a molecular weight of 29,000 Daltons, is the major viral encoded structural protein of the viral occlusions.

Since the viral occlusions provide a means for stable horizontal transmission, they are an important part of the natural virus life cycle. When infected larvae die, millions of polyhedra are left within the decomposing tissue. The viral occlusions aid in protecting the embedded virus particles from environmental factors that would otherwise rapidly inactivate ECV. When larvae feed on contaminated plants, they ingest the polyhedra. The occlusions dissolve in the alkaline environment of the insect gut, releasing virus that invade and replicate in the cells of the midgut tissue.

Secondary infection spreads to other insect tissues by the extracellular viral (ECV) route. Virus particles enter the cell by endocytosis or fusion and the viral DNA is uncoated. DNA replication occurs at about 6 hours post-infection (pi) and by 10 hours pi, extracellular virus is released from the cell by budding. Polyhedrin protein can be detected by 12 hours pi but viral occlusions are not readily detected until 18–24 hours pi. Extracellular virus levels reach a maximum between 36–48 hours pi and the polyhedrin protein continues to accumulate for 4–5 days until the infected cells lyse.

Baculovirus Expression Vectors (BEVs)

Baculovirus expression vectors (BEVs) have become extremely important tools for the expression of foreign genes, both for basic research and for the production of proteins with direct clinical applications in human and veterinary medicine. BEVs are recombinant insect viruses in which the coding sequence for a desired foreign gene has been inserted 3' to a select baculovirus promoter, e.g. the polyhedrin promoter in place of the non-essential viral gene, polyhedrin, thereby promoting the expression of the chosen foreign gene. (V. A. Luckow and M. D. Summers, *Bio/Technology*, 6:47–55 (1988a); M. D. Summers, *Curr. Commun. in Molec. Biol.*, Cold Spring Harbor Press. Cold Spring Harbor, N.Y. (1987), Summers, M. D. and Smith, G. E., TAES Bulletin No. 1555, (1988); Smith and Summers, U.S. Pat. Nos. 4,745,051 and 4,040,367); Webb and Summers, In Press, Techniques, 1990).

Several advantages may be enjoyed when employing the exemplary baculovirus expression vector (BEV) system. One of these advantages is the strong polyhedrin promoter which directs a high level of expression of the foreign insert (protein of choice). The newly expressed protein accumulates in large amounts within these infected insect cells or as secreted products. Thus, as a result of the relative strength of the polyhedrin promoter, many different desired foreign gene inserts can be expressed at very high levels.

In addition to providing a high expression level, another advantage of the BEV system, is the ease with which these baculoviruses are produced and identified. This process begins by co-transfecting wild-type viral DNA and a "transfer vector" into susceptible host cells. A transfer vector is defined as a bacterial plasmid which contains a foreign gene directly 3' to a desired baculovirus promoter, e.g. the polyhedrin promoter, as well as long viral sequences flanking the promoter on the 5' side and the foreign gene on the 3' side. During cotransfection, homologous recombination occurring between viral and transfer vector DNA will produce a small percentage of viral genomes in which the polyhedrin gene has been replaced by the foreign gene (less than 5%). The wild-type progeny can be differentiated from the recombinant progeny by a conventional viral plaque assay. Recombinants in which the polyhedrin gene has been replaced, can be identified by their occlusion-negative plaque phenotype observed on a background of occlusion-positive wild-type plaques.

Because the polyhedrin gene is a non-essential gene for productive viral infection, another advantage of baculovirus expression vectors is that the recombinants are viable, helper-independent viruses. Also, baculoviruses are known to infect arthropods of which the Lepidopteran insects comprise the largest group of susceptible species. Thus, they are noninfectious for vertebrates, and are therefore relatively safe genetic manipulation agents.

Thus, baculoviruses have gained popularity as expression vectors because of the advantages presented above. The BEV system is currently being employed by numerous investigators for the over expression and production of many different foreign gene products. To date, more than 175 different genes have now been expressed by employing this system (Luckow, V. A., and M. D. Summers, Bio/Technology 6:47-55 (1988)).

Recombinant proteins produced in the BEV system retain many of their authentic biological properties including intracellular targeting, secretion and receptor binding (Luckow and Summers, 1988, Id.; Webb and Summers, In Press, Techniques, 1990). In terms of processing, most recombinant protein products appear to undergo normal post-translational modifications such as proteolytic processing of polyprotein precursors, removal of signal sequences and chemical modifications including glycosylation and phosphorylation.

The recombinant baculovirus infected insect cells would therefore serve as an ideal model for the production of a variety of different types of proteins, vaccines, antigens or immunogens.

Temporal Regulation of Baculovirus Genes

Baculovirus genes are expressed in a sequential, temporally-regulated fashion during one or more of the different phases of the viral replication cycle (L. A. Guarino, and M. D. Summers, *Journal of Virology*, 57(2):563-571 (1986); Guarino, L. A. and Summers, M. D., *Journal of Virology*, 61(7):2091-2099 (1987)). Therefore, depending on their temporal expression during viral infection, different baculovirus genes are classified as immediate-early, delayed-early, late or very late.

The expression of these genes occurs sequentially, probably as the result of a 'cascade' mechanism of transcriptional regulation. In other words, the immediate-early genes are expressed immediately after infection and expression may occur in the absence of other viral functions. One or more of the resulting gene products in turn induces transcription of the delayed-early genes. Continuing in the cascade, some delayed-early gene products induce transcription of late genes and finally the very late genes are expressed under the control of the previously expressed gene products from one or more of the earlier temporal classes of genes.

One relatively well defined component of this regulatory cascade is IE1, an immediate-early gene of *Autographa californica* nuclear polyhedrosis virus. IE1 is expressed in the absence of other viral functions and encodes a product that stimulates the transcription of several genes of the delayed-early class, including 39K gene, as well as late genes (early genes: L. A. Guarino and M. D. Summers, *J. Virol.*, 57:563-571 (1986a); *J. Virol.*, 61:2091-2099 (1987); late genes: L. A. Guarino and M. D. Summers, *Virol.*, 162:444-451 (1988)).

In contrast to the IE1 gene, the polyhedrin gene is classified as a very late gene. Thus, transcription from the polyhedrin promoter requires the previous expression of an unknown number of other viral and/or cellular gene products. Thus, the exemplary BEV system described by Smith and Summers (U.S. Pat. No. 4,745,051) will express foreign genes only as a result of gene expression from the earlier expressed portion of the viral genome and only after the viral infection is well underway.

Construction of Recombinant Baculovirus Expression Vectors

General methods for handling and preparing baculovirus vectors and baculoviral DNA, as well as insect cell culture procedures, are outlined in *A Manual of Methods for Baculovirus Vectors and Insect Cell Culture Procedures* (Summers, M. D. and G. E. Smith, TAES Bulletin No. 1555, 1988). Homologous recombination, plaque selection, purification and propagation procedures as well as cotransfection protocols are known to those familiar and skilled in this art.

Bacterial transformation, screening by restriction mapping, extraction, construction of bacterial transfer vectors, purification of bacterial plasmid DNA, as well as other standard molecular biology procedures, will be accomplished by standard recombinant DNA techniques (Maniatis, et al, *Molecular cloning: A laboratory manual*, Cold Spring Harbor Press, Cold Spring Harbor, N.Y. (1982)).

It should be emphasized that the experimental procedures described below represent examples of how genes are cloned and expressed at different time points post infection (p.i.) in baculovirus infected insect cells. Standard recombinant procedures are used for the construction of recombinant plasmids (Maniatis et al, 1982) as well as for the generation and propagation of recombinant baculovirus strains (Summers and Smith, 1987).

The examples which follow are illustrative of laboratory techniques found by the present inventor to constitute preferred modes for practicing various aspects of the invention. However, those of skill in the art, in light of the present disclosure, will appreciate that various modifications and alterations can be made in the structuring and carrying out of the invention, and still remain within the spirit and scope of the invention.

EXAMPLE 1

Model Baculovirus Expression Vector Containing Three Baculovirus Promoters for Either Recombinant Protein, Virus, Protein Hybrid or Virus Hybrid Production The construction of a model expression vector which would be employed for recombinant protein, virus, protein hybrid or virus hybrid production is diagramed.

FIG. 1 outlines the minimal essential features needed for the production of either a recombinant virus, protein, virus hybrid or protein hybrid. Desired genes are inserted 3' to either the late or the early baculovirus promoters. This bacterial transfer vector will recombine homologously at 13.0 map units in the nonessential region of wild type baculovirus. The potential combinations for the different genes and their modifications are numerous.

For the production of different viruses or vaccines, the transfer vector can be designed to contain cDNA encoding truncated non-structural genes positioned 3' to an early baculovirus gene promoter while the genes coding for the structural proteins are positioned adjacent the late baculovirus promoter, e.g. the polyhedrin gene promoter. The details for the production of different viruses, vaccines, or virus hybrids are described below.

In general, recombinant baculovirus DNA of choice is produced by cotransfection of Sf9 cells with a specifically designed and constructed transfer vector and wild type viral DNA (FIG. 1). This specifically designed transfer vector can be used for the production of many different proteins, viruses, protein hybrids, or virus hybrids. One of the many novel concepts for using a specifically designed recombinant baculovirus expression vector involves combining structural and non-structural genes from two different viral sources for the purpose of designing, and thereby producing, an essentially different hybrid viral particle. The specifically designed transfer vector may be used for producing many different compositions.

Minimal essential features of the model baculovirus expression vector are:

1. Natural Polyhedrin Promoter/desired gene: designates a late baculovirus polyhedrin promoter with or without a desired gene of choice inserted 3' to the polyhedrin promoter. 3' is defined as the region located downstream of the compared component. This natural polyhedrin promoter is located within Eco-RI Fragment I and is useful for stabilizing the virus in the environment by conferring resistance to inactivation.

2. Late Promoter/desired gene: designates a baculovirus late promoter with a desired gene of choice inserted 3' to the polyhedrin promoter. 3' is defined as the region located downstream of the compared component.

This promoter and gene complex will be recombined at a nonessential region into wild type baculovirus. A non-essential region of the baculovirus genome is defined as a place where insertion or modification of natural viral DNA sequence or gene structure has no effect on infectivity of the modified virus in cell culture. The site for recombination can be any one available, however, the inventors prefer the non-essential 13.0 map unit site of wild type baculovirus.

Many different combinations of a late promoter with a desired gene are available. For example, for the late promoter, any baculovirus late promoter will suffice, however, the inventors prefer to employ the promoter from either polyhedrin or p10 gene. The desired gene can feasibly be derived from any eukaryote or prokaryote.

3. Early Promoter/desired gene: designates a baculovirus early promoter with a desired gene of choice inserted 3' to the polyhedrin promoter. 3' is defined as the region located downstream of the compared component.

This promoter and gene complex will be recombined at a nonessential region into wild type baculovirus (as described above). A non-essential region of the baculovirus genome is defined as a place where insertion or modification of natural viral DNA sequence or gene structure has no effect on infectivity of the modified virus in cell culture. The site for recombination can be any one available, however, the inventors prefer the 13.0 non-essential map unit region of wild type baculovirus.

Many different combinations of an early promoter with a desired gene are available. The early gene promoter region isolated from baculovirus may be an immediate-early gene of the virus such that no additional viral gene or gene product is needed in order to get constitutive expression of the heterologous gene. The immediate-early gene from which the promoter region is derived may be either IE1 or IEN. In a preferred embodiment, the gene promoter region is isolated from the immediate-early gene of baculovirus, IE1 or IEN.

IE1 may be expressed in the absence of other viral functions and encodes a product that stimulates the transcription of several genes of the delayed-early class, including the 39K gene (L. A. Guarino and M. D. Summers, *J. Virol.*, 57:563–571 (1986a); *J. Virol.*, 61:2091–2099 (1987)).

An immediate-early gene as described above is used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII-k fragment of the baculovirus genome. In a preferred embodiment, the 39K promoter region is linked to the heterologous gene of interest and expression is further controlled by the presence of IE1.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

Again, the desired gene positioned to the early baculovirus promoter can feasibly be derived from any eukaryote or prokaryote.

This model baculovirus expression vector is essentially comprised of three baculovirus promoters. Two of the three promoters are homologously recombined into the 13.0 map unit non-essential region of wild type baculovirus.

Figure 1B:
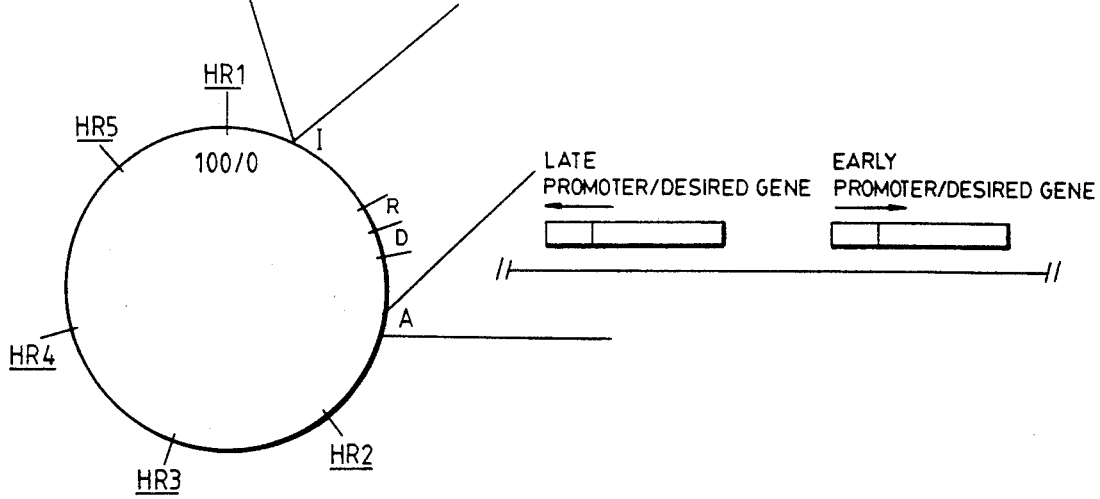

FIG. 1B demonstrates one of the many different combinations that may be employed in this model baculovirus expression vector. This model expression vector contains three baculovirus promoters adjacent to desired genes and serves as an example only. The first polyhedrin promoter appears in its natural site within Eco-RI Fragment I. The second promoter is a polyhedrin promoter, adjacent and 5' to a desired gene, inserted through homologous recombination into a non-essential region of the baculovirus genome. The arrow indicates the direction the promoter expresses the adjacent DNA. Also, inserted through homologous recombination into this non-essential region of the genome, is a third promoter. This third promoter is an early or immediate early baculovirus promoter, for example IE1, 39K or IEN. In this example, the immediate early baculovirus promoter, IE1, is adjacent to a desired gene and the promoter directs the expression of the desired gene (indicated by the arrow). The two promoters in the non-essential region of the genome are expressed in opposite directions. Non-essential region of the baculovirus genome is defined as above.

EXAMPLE 2

Construction of New AcMNPV Transfer Vectors Containing Both Early and Late Baculovirus Promoters The development of recombinant viruses that are optimally infectious in insect larvae requires encapsulation of these viruses into viral occlusions. The integrity of the polyhedrin gene in the recombinant virus must therefore be left intact. A region of the AcMNPV genome which is separate from the polyhedrin gene and which is non-essential for the replication and infection of AcMNPV in vivo and in vitro has been identified (Gonzalez, Smith and Summers, 1989, Virology 170: 160-175).

FIG. 2A schematically represents a transcription map of AcMNPV. The gene products are indicated above the horizontal line. At least 15 different gene products are indicated by the bold, filled in arrow heads. Examples of gene products are: Polyhedrin, egt, V-ubi, 39K, ETL, 25K, DNA polymerase, capsid, etc.

Arbitrary designation of map units for the fragments generated from the restriction enzyme Eco-RI are indicated by small numbers below the solid horizontal line. Zero map units start at the right of "HR1" and 100 map units ends at the left of "HR1."

Enhancer sequences are numbered numerically HR1, HR2, HR3, HR4, or HR5 for convenience. When a combination of immediate-early genes and a delayed-early gene promoter region is employed, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. In a preferred embodiment, the hr5 enhancer sequence is linked directly (in cis) to the delayed-early gene promoter region, 39K, thereby enhancing the expression of the cloned heterologous DNA.

Fragments generated by the restriction enzyme Eco-RI are assigned letters according to size ("Fragment A" is the largest, "B" is the next largest, "C" is the next largest, etc.; I, R, D, A, J, K, T, M, N, F, V, U, C, G, W, D, Q, L, E, H, S, X, P, and B)

The region where pSfHindIII-L will recombine into the AcMNPV [.d10A] polyhedrin deletion mutant is designated by the wedged pie area and designated FIG. 2B.

Recombination of pSfHindIII-L into the AcMNPV.d10A polyhedrin deletion mutant is diagramed in FIG. 2B. Only AcMNPV.EcoR1-A and the physical alterations of the fragment are shown. The majority of Pst1-O was deleted and a 3.7 kb fragment from pSfHindIII-L is inserted in its place. Horizontal lines represent transcripts and their orientation. Dashed lines indicate possible termination sites. Genomic map units (m.u.) are shown at specific sites beneath correlating fragment dimensions. The wedged pie area is magnified in subsequent figures to present more detail.

FIG. 2B describes the recombination of pSfHindIII-L into the AcMNPV.d10A polyhedrin deletion mutant. Only AcMNPV.EcoR1-A and the physical alterations of the fragment are shown. This figure also depicts the non-essential region that has been mapped to the EcoRI-A fragment (13.4-14.7 map units) of the ACMNPV genome. The insertion of foreign DNA into this region results in occlusion-positive viruses which are infectious in vivo (Gonzalez et al, 1989). This nonessential 13.2 map unit region of the AcMNPV genome is designated the "13.0 map unit region" for simplicity. The definition of the 13.0 map unit region of the AcMNPV genome is meant to include 13.2 map units.

The majority of Pst1-O was deleted and a 3.7 kb fragment from pSfHindIII-L is inserted in its place (FIG. 2B). Horizontal lines represent transcripts and their orientation. Dashed lines indicate possible termination sites. Genomic map units (m.u.) are shown at specific sites beneath correlating fragment dimensions.

Isolation of the Ac/Sf Hybrid Virus

The AcMNPV mutant d 10A was used to construct a recombinant virus containing a heterologous polyhedrin gene. The AcMNPV d 10A lacks approximately 25% of the polyhedrin coding region and produces a truncated polyhedrin protein of 20 kDa (Smith et al., 1983b), thus, producing occlusion-negative (occ-) plaques. The SfMNPV polyhedrin gene was localized to the 4.0-kb HindIII-L fragment of SfMNPV DNA by Southern hybridization using the AcMNPV -HindIII-V fragment as a probe. A recombinant plasmid containing the SfMNPV HindIII-L fragment was then cotransfected with AcMNPV d 10A DNA. This resulted in occlusion-positive plaques which were marked and further plaque-purified. Occlusive-positive plaques were detected at a frequency of 1 in every 10,000 plaques.

Cloning Strategy

Foreign DNA may be directed into specific regions of the AcMNPV genome by flanking the foreign DNA with viral sequences that are homologous to the targeted region. The foreign DNA is inserted into the targeted region by homologous recombination. To construct transfer vectors that will direct homologous recombination to the 13.2 map-unit region of the AcMNPV genome, a 4.3 kb Bgl II fragment derived from the EcoR1-A fragment was cloned into a pUC9 plasmid vector. A unique XbaI site located in this fragment is used for the insertion of foreign DNAs so that 2.4 kb and 1.9 kb of EcoR1-A sequence flank the 5' and 3' ends of the inserted DNA.

Expression of foreign genes may be temporally regulated by using viral promoters which are active at different times during the course of infection. To express proteins both early and late in infection, the immediate early IE1 promoter and the very late polyhedrin promoter were chosen for the new transfer vector constructs.

EXAMPLE 3

Construction of Transfer Vector RIA-1392

FIG. 3 depicts transfer vector RIA-1392. For late expression, foreign genes which contain a translation start signal may be inserted into the Bgl II site of RIA-1392. The line drawing indicates that RIA-1392 will homologously recombine into the non-essential 13.0 map unit region of Fragment A of the AcMNPV genome.

RIA-1392 contains a unique Bgl II site for the insertion of foreign genes under the control of the polyhedrin promoter. Sequences containing a modified polyhedrin promoter, a portion of the polyhedrin open reading frame, and the polyhedrin polyadenylation signal are inserted at the XbaI site in the transfer vector construct designated "RIA-1392." RIA-1392 contains a unique Bgl II cloning site for the insertion of foreign genes located at +35 in relation to a mutated polyhedrin translation start signal. RIA-1392 also contains the B-glucoronidase gene under the control of the polyhedrin promoter for use as a selectable marker. This transfer vector contains 1.9 kb (PstI-XbaI 1.9 kb non-essential region of AcMNPV genome at 13.4 map unit of Eco-RI-A viral flanking sequences) and 2.4 kb (Bam HI-XbaI non-essential region of AcMNPV genome at 13.4 map units of EcoR1-A viral flanking sequences) of Eco-RI-A viral flanking sequences.

The cloning steps for construction of this vector are:
1. Subclone the 4.3 kb BGIII fragment of the AcMNPV EcoRI-A region into BamH1-digested pUC9. This construct is designated pUC9/RIA-BgIII.
2. Mutate the XbaI site of pVLI392 by digesting with XbaI, filling in with Klenow, and religating. The resulting construct is designated 1392(-Xba).
3. Partially digest 1392(-Xba) with HindIII and completely digest with EcoRV. Isolate the 1.1 kb HindIII-EcoRV fragment, which contains the polyhedrin promoter, a polylinker for the insertion of foreign genes located 35 bp downstream from a mutated translation start signal, a portion of the polyhedrin open reading frame, and a polyadenylation signal. Insert this fragment into HindIII and HindII-digested Bluescript. The resulting construct is designated Bst/1392.
4. Insert the 2.2 kb BamHI fragment from pVLIO62, which contains the 13-glucuronidase open reading frame, into the Bgl II site of Bst/1392. A subclone containing the B-glucuronidase insert in the proper orientation in relation to the polyhedrin promoter is designated Bst/1392-Bgluc.
5. In a three-way ligation, combine the ~1.1 kb XbaI-ApaI fragment of Bst/1392, the ~3.3 kb Spe-ApaI fragment of Bst/1392-Bgluc and XbaI-digested pUC9/RIA-BgIII. The resulting construct is designated RIA-1392.

The direction in which the promoter directs transcription of the adjacent gene is indicated by arrows.

To facilitate the selection and purification of recombinant occ+ baculoviruses, the gene encoding B-glucuronidase (Jefferson, Burgess, and Hirsch, 1986, pNAS 83:8447-8451) under the control of the polyhedrin promoter is inserted into the transfer vectors in the opposite orientation to the foreign gene. Because the foreign gene is on the same plasmid as B-glucuronidase, cells which acquire the foreign gene will also acquire the marker gene. Thus, the addition of the chromogenic dye 5-bromo-4-chloryl-3-indolyl-B-D-galactopyranoside (X-gal) may be used to identify recombinant plaques in a baculovirus plaque assay.

EXAMPLE 4

Construction of Transfer Vector RIA-IEI

Construction of transfer vector RIA-IE1 is depicted in FIG. 4. For immediate early expression, foreign genes which contain a translation start signal may be inserted into the Bgl II site of RIA-IE1. The line drawing indicates that RIA-IE1 will homologously recombine into the non-essential 13.0 map unit region of Fragment A of the AcMNPV genome.

Sequences containing a modified IE1 promoter, a portion of the IE1 open reading frame, and the IE1 polyadenylation signal are inserted at the XbaI site in the transfer vector construct designated "RIA-IEI." RIA-IE1 contains a unique Bgl II site for the insertion of foreign genes under the control of the IE1 promoter. Foreign genes are inserted at −39 in relation to the IEI translation start ATG. RIA-IE1 also contains the B-glucoronidase gene under the control of the polyhedrin promoter for use as a selectable marker. This transfer vector contains 1.9 kb (PstI-XbaI 1.9 kb non-essential region of AcMNPV genome at 13.4 map unit of Eco-RI-A viral flanking sequences) and 2.4 kb (Bam HI-XbaI non-essential region of AcMNPV genome at 13.4 map units of EcoR1-A viral flanking sequences) of Eco-RI-A viral flanking sequences.

The cloning steps for construction of this vector are:
1. Isolate the ~1.8 kb BamHI-SpeI fragment from IE1(−)39Bgl II. This fragment contains a modified IE1 promoter containing a Bgl II site 35 bp upstream from the IE1 translation start signal, a portion of the IE1 open reading frame, and a polyadenlyation signal. Subclone this fragment into BamHI and SpeI digested Bluescript. The resulting construct is designated Bst/IE1.
2. Replace the 1.1 kb Apa-SpeI fragment of RIA-1392 with the 1.8 kb Apa-Spe fragment from Bst/IE1. The resulting construct is designated RIA-IE1.

The direction in which the promoter directs transcription of the adjacent gene is indicated by arrows.

To facilitate the selection and purification of recombinant occ+ baculoviruses, the gene encoding B-glucuronidase (Jefferson, Burgess, and Hirsch, 1986, PNAS 83:8447-8451) under the control of the polyhedrin promoter is inserted into the transfer vectors in the opposite orientation to the foreign gene. Because the foreign gene is on the same plasmid as B-glucuronidase, cells which acquire the foreign gene will also acquire the marker gene. Thus, the addition of the chromogenic dye 5-bromo-4-chloryl-3-indolyl-B-D-galactopyranoside (X-gal) may be used to identify recombinant plaques in a baculovirus plaque assay.

EXAMPLE 5

Construction of Transfer Vector RIA-39K

The construction of transfer vector RIA-IE1 is depicted in FIG. 5. The line drawing indicates that RIA-39K will homologously recombine into the non-essential 13.0 map unit region of Fragment A of the AcMNPV genome. RIA-39K contains a unique Bgl II site for the insertion of foreign genes under the control of the 39K promoter. Foreign genes are inserted at −80 in relation to the 39K translation start codon. RIA-39K also contains the B-glucuronidase gene under the control of the polyhedrin promoter for use as a selectable marker. This transfer vector contains 1.9 kb (PstI-XbaI 1.9 kb non-essential region of AcMNPV genome at 13.4 map unit of Eco-RI-A viral flanking sequences) and 2.4 kp (Bam HI-XbaI non-essential region of AcMNPV genome at 13.4 map units of EcoR1-A viral flanking sequences) of Eco-RI-A viral flanking sequences. The direction in which the promoter directs transcription of the adjacent gene is indicated by arrows.

The cloning steps for construction of this vector are:
1. Digest 39CAT with BamHI, fill-in with Klenow, and ligate to Bgl II linkers. Digest the resulting DNA with Bgl II and FspI. Isolate the 330 bp Bgl II-Fsp fragment, which contains a modified 39K promoter and 3' viral sequences. Excise the ApaI-Bgl II fragment from RIA-1392 and replace it with the 330 bp 39K fragment.

To facilitate the selection and purification of recombinant occ+ baculoviruses, the gene encoding B-glucuronidase (Jefferson, Burgess, and Hirsch, 1986, PNAS 83:8447-8451) under the control of the polyhedrin promoter is inserted into the transfer vectors in the opposite orientation to the foreign gene. Because the foreign gene is on the same plasmid as B-glucuronidase, cells which acquire the foreign gene will also acquire the marker gene. Thus, the addition of the chromogenic dye 5-bromo-4-chloryl-3-indolyl-B-D-galactopyranoside (X-gal) may be used to identify recombinant plaques in a baculovirus plaque assay.

EXAMPLE 6

Construction of Transfer Vector RIA-1392CAT

Figure 6:
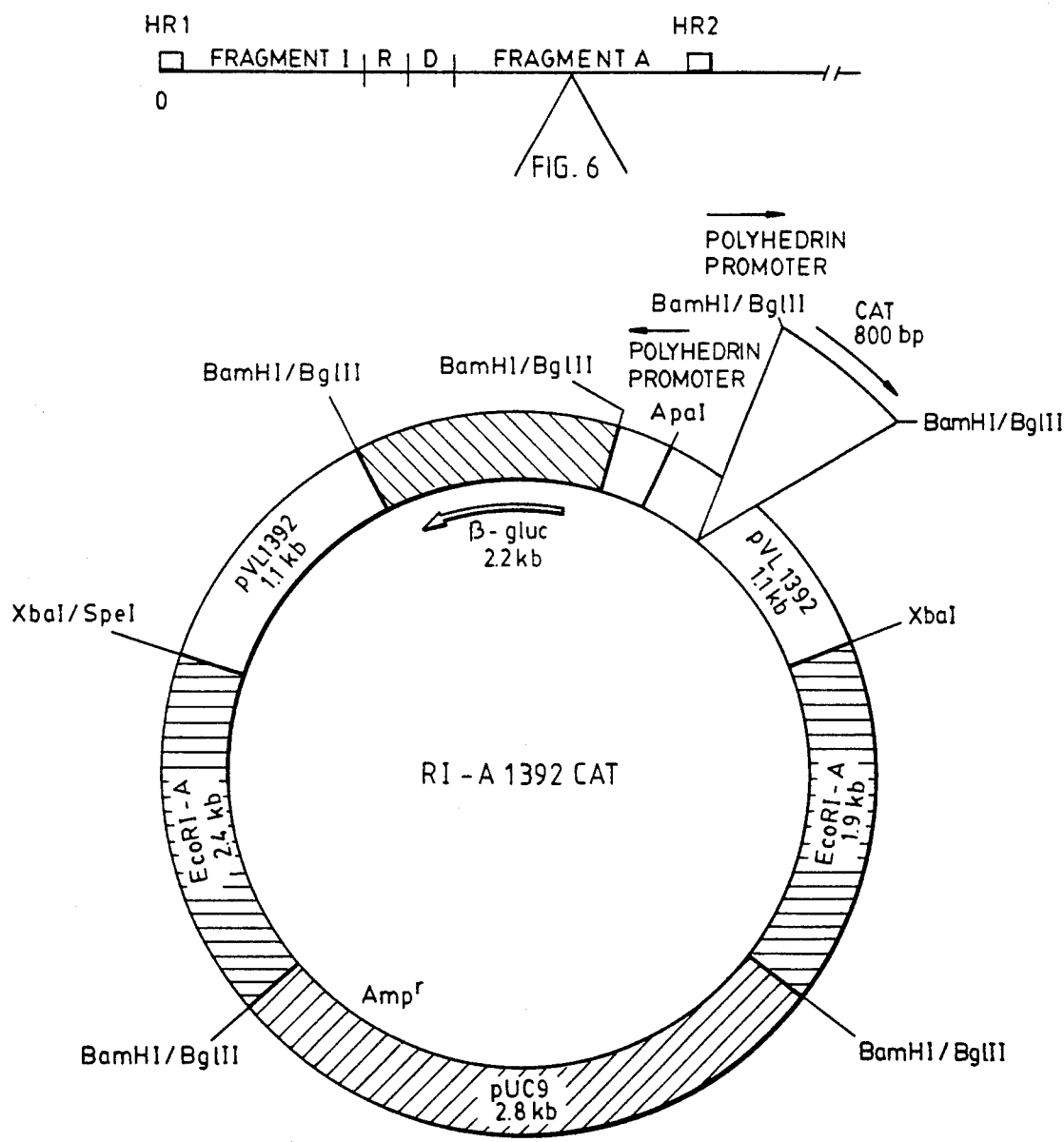

The construction of transfer vector RIA-1392CAT is depicted in FIG. 6. The line drawing indicates that RIA-1392CAT will homologously recombine into the non-essential 13.0 map unit region of Fragment A of the AcMNPV genome. The direction in which the promoter directs transcription of the adjacent gene is indicated by arrows.

Construct RIA-1392CAT contains the chloramphenicol acetyl transferase gene (CAT) under the control of one polyhedrin gene and the b-glucoronidase gene under the control of a second polyhedrin gene for use as a selectable marker. This transfer vector contains 1.9 kb (PstI-XbaI 1.9 kb non-essential region of AcMNPV genome at 13.4 map unit of Eco-RI-A viral flanking sequences) and 2.4 kp (Bam HI-XbaI non-essential region of AcMNPV genome at 13.4 map units of EcoR1-A viral flanking sequences) of Eco-RI-A viral flanking sequences.

Initial studies to examine the ability of this transfer vector to direct the insertion of foreign genes into the 13 map unit region of the AcMNPV genome, and to evaluate the stability of recombinant viruses obtained from these transfer vectors are planned. The expression level produced by these transfer vectors will be compared to the expression obtained from conventional transfer vectors (i.e. pVL941) using the reporter gene CAT.

To facilitate the selection and purification of recombinant occ+ baculoviruses, the gene encoding B-glucuronidase (Jefferson, Burgess, and Hirsch, 1986, pNAS 83:8447-8451) under the control of the polyhedrin promoter is inserted into the transfer vectors in the opposite orientation to the foreign gene. Because the foreign gene is on the same plasmid as B-glucuronidase, cells which acquire the foreign gene will also acquire the marker gene. Thus, the addition of the chromogenic dye 5-bromo-4-chloryl-3-indolyl-B-D-galactopyranoside (X-gal) may be used to identify recombinant plaques in a baculovirus plaque assay.

EXAMPLE 7

Construction of Vector RIA-IE1CAT

The construction of transfer vector RIA-IE1CAT is depicted in FIG. 7. The line drawing indicates that RIA-IE1CAT will homologously recombine into the non-essential 13.0 map unit region of Fragment A of the AcMNPV genome. The direction in which the promoter directs transcription of the adjacent gene is indicated by arrows.

Figure 8:
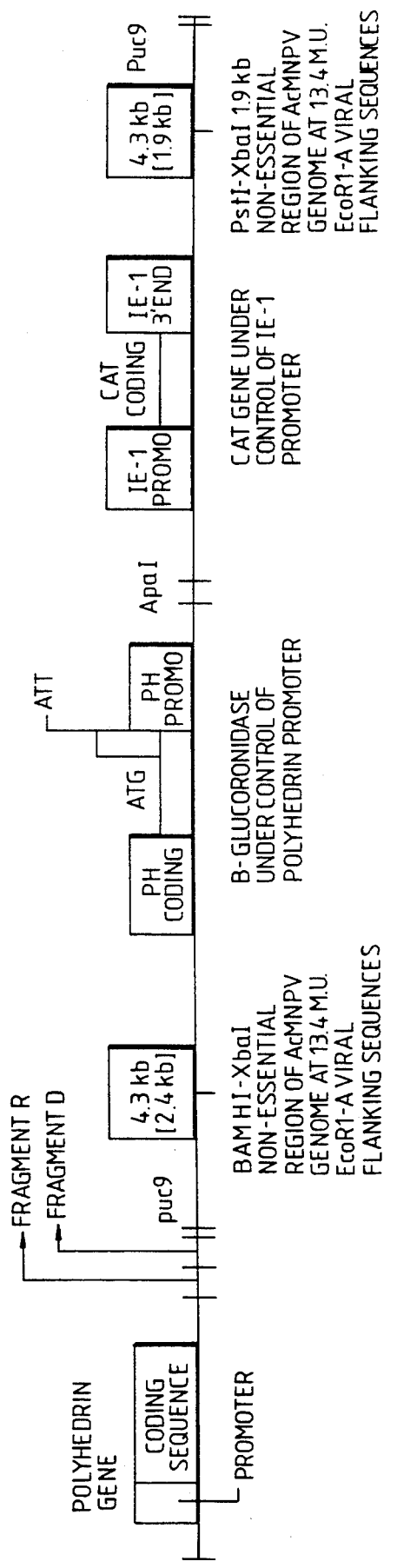

Construct RIA-IE1CAT contains the chloramphenicol acetyl transferase gene (CAT) under the control of the IE1 promoter and the B-glucuronidase gene under the control of the polyhedrin promoter for use as a selectable marker (FIG. 7). This transfer vector contains 1.9 kb (PstI-XbaI 1.9 kb non-essential region of AcMNPV genome at 13.4 map unit of Eco-RI-A viral flanking sequences) and 2.4 kp (Bam HI-XbaI non-essential region of AcMNPV genome at 13.4 map units of EcoR1-A viral flanking sequences) of Eco-RI-A viral flanking sequences. Linear representation of vector RIA-IE1CAT is shown in FIG. 8.

Initial studies to examine the ability of these transfer vectors to direct the insertion of foreign genes into the 13 map unit region of the AcMNPV genome, and to evaluate the stability of recombinant viruses obtained from these transfer vectors are planned. The expression level produced by these transfer vectors will be compared to the expression obtained from conventional transfer vectors (i.e. pVL941) using the reporter gene CAT.

To facilitate the selection and purification of recombinant occ+ baculoviruses, the gene encoding B-glucuronidase (Jefferson, Burgess, and Hirsch, 1986, PNAS 83:8447-8451) under the control of the polyhedrin promoter is inserted into the transfer vectors in the opposite orientation to the foreign gene. Because the foreign gene is on the same plasmid as B-glucuronidase, cells which acquire the foreign gene will also acquire the marker gene. Thus, the addition of the chromogenic dye 5-bromo-4-chloryl-3-indolyl-B-D-galactopyranoside (X-gal) may be used to identify recombinant plaques in a baculovirus plaque assay.

EXAMPLE 8

Homologous Recombination of a Desired Recombinant Baculovirus Transfer Vector into the 13.0 Map Unit Nonessential Region of Wild Type Baculovirus FIG. 9 diagrams the homologous recombination of a desired recombinant baculovirus transfer vector into the 13.0 map unit nonessential region of wild type baculovirus. The construction of different bacterial transfer vectors are described in the examples above. The transfer vectors described above (RIA-1392, RIA-IE1, RIA-39K, RIA-1392 CAT, RIA-IE1 CAT) are used as examples only. Any other desired promoter and gene complex may be employed with equal success. The polyhedrin-beta-glucoronidase containing recombinant baculovirus produces blue plaques. This selectable marker allows for easy identification of desired recombinants (via observing blue plaques). Once Sf9 cells are infected with the desired recombinant, this desired recombinant may further be propagated, isolated, and purified. These protocols are known and standard for one of ordinary skill in the art.

EXAMPLE 9

Genetic Engineering of a Non-Replicative Virus or Virus Hybrid Using the Baculovirus as a Tool Viral Infections and Vaccines The number of known viral infections that infect humans and animals is too numerous to list. The necessity to control or abate viral infections has been a major medical concern for many decades. Basically, the eradication and/or control of viral infections involves the production of a variety of different and highly potent vaccines. Quantitative production of pure and potent viral antigens or immunogens is difficult as well as expensive. This is usually due to the fact that many viruses replicate very slowly, if at all, in controlled cell culture environments. If the virus of choice seldom replicates in the test tube, then the production of the specific viral particle becomes less favorable and effective as well as more expensive.

The classical method for producing vaccines against viral pathogens is to "attenuate" the virus. Attenuation is a process of diminution of viral virulence in an organism. This diminution is generally obtained through the selection of variants which occur naturally or through experimental manipulation. With attenuation, the virus remains infective and self-replicative but does not cause the symptomatic disease. Because attenuation does not generally alter the replicative capacity of the virus, drawbacks arise. Attenuation is therefore not favored because the introduction of live attenuated vaccines into humans, as well as are the risks involved in handling the attenuated vaccines, may be hazardous.

Another approach for the production of viral antigen and/or immunogen is to synthesize single proteins of the derived viral particle or portions thereof. Thus, the aim is to elicit an appropriate immune response or reaction without the danger of viral replication (viremia). The production of so called "Subunit" vaccines or diagnostic reagents has been achieved by using a variety of different expression vector systems as well as by chemical synthesis of the corresponding peptide sequences of importance (putative antigenic or immunogenic epitopes). However, subunit vaccines are for most of the part much less potent and less protective as compared to attenuated whole virus particles.

Thus, there is a strong need for the production of vaccines and diagnostics that are potent, safe to use and also economical to produce. Therefore, it is the intent of this invention to produce vaccines and diagnostics which are potent, safe to use as well as economical to produce, thereby filling the void in the area of clinical medicine and research. Production of potent vaccines is a necessity for this field to advance. The synthesized vaccine must closely represent the authentic pathogen (e.g. mimic the virus particle) without being harmful in clinical use. These characteristics are naturally advantageous also when diagnostic reagents are concerned.

Genetic Engineering of a Non-Replicative Virus Using the Baculovirus as a Tool

FIG. 10A depicts the construction of a non-replicative baculovirus virus wherein the non-structural genes are truncated or mutated. The source of the viral genome structural and non-structural genes are the same. Sindbis virus is used as an example only. The non-structural genes are mutated or truncated in such a manner that capsid formation is possible whereas the structural proteins are intact (capsid, E1, E2).

Wild-type replicative Sindbis RNA is represented by a darker line as compared to the line representing truncated non-replicative Sindbis RNA. The structural Sindbis proteins E1 and E2 are represented by large open circles. Since the respective proteins are successively synthesized, and therefore temporally regulated, the truncated non-replicative non-structural RNA, whose synthesis is driven by an early baculovirus promoter, is synthesized prior to the structural proteins (whose synthesis is driven by a late baculovirus promoter). This temporal regulation of transcription allows for the proper assembly of the virus particle constructed from one recombinant baculovirus.

Strategy for Synthesizing a Non-Replicative Sindbis Virus Particle in an Insect Cell Using Baculovirus Vectors The genes encoding the non-structural proteins (ns) have to be modified to either inactive the translation protein products or simply alter the translation start site of the intact messenger by mutation (e.g. mutation of the AUG). An example of inactivation would be deletion of essential sequences within single genes. This is merely one example and those skilled in this art know that alternate methods exist. although The latter possibility would make an almost identical genome as compared to the wild-type but the messenger can not be translated. Consequently, non-structural proteins would not be synthesized and the genome would be non-replicative. In addition the RNA sequence of the genome specifying the 26S subgenomic RNA, i.e.d the coding sequence for the structural proteins would be deleted. The modifications, however, have to be made so that the capsid protein still is capable of forming the complex with the "remaining mutated genomic RNA", formation of the capsid itself, in order for the final virus particle to be assembled. The result is a piece of genomic RNA that can not replicated within the cell but still has the properties needed for capsid formation.

The "remaining genomic cDNA" is placed under the transcriptional regulation of e.g. the baculovirus IE1 promoter and the complete 26S cDNA is driven by the baculovirus polyhedrin gene promoter. Thus the result is a Sindbis virus particle which is synthesized during recombinant baculovirus infection. The particle has the same antigenic properties as its authentic infectious counterpart, but can not replicate in the cell.

Genetic Engineering of a Non-Replicative Virus Hybrid Using the Baculovirus as a Tool FIG. 10B HYBRID is a schematic representation of constructing a non-replicating virus hybrid. The non-replicative aspect results from truncating the RNA encoding the non-structural genes. The virus hybrid is constructed by producing non-structural genes from Virus A and structural genes from Virus B. Truncated Sindbis non-structural genes and structural Rubella genes are used as examples only.

As depicted in FIG. 10B HYBRID, the non-structural genes are from Sindbis virus and the structural genes are from Rubella virus. The Sindbis non-structural genes are mutated or truncated in such a manner that encapsidation is possible. The Sindbis capsid protein is represented by small closed circles. The structural genes encoding for the Sindbis capsid protein and Rubella virus envelope glycoproteins remain intact, while the genomic RNA is genetically mutated or truncated by standard techniques known to those skilled in the art. Wild-type replicative Sindbis RNA is represented by a darker line as compared to the line representing truncated non-replicative Sindbis RNA.

The structural Sindbis envelope proteins E1 and E2 are represented by large open circles whereas the corresponding envelope proteins of Rubella virus are illustrated by large shaded circles thereby generating what is termed the virus hybrid particle. Since the respective proteins are temporally regulated, and therefore successively synthesized, the truncated non-replicative Sindbis non-structural RNA, whose synthesis is driven by an early baculovirus promoter, is synthesized prior to the structural Sindbis and Rubella proteins (whose synthesis is driven by a late baculovirus promoter). This temporal regulation of transcription allows for the proper assembly of the virus hybrid particle comprised of non-structural genes from Sindbis virus and Rubella virus structural genes.

The novel construction of a non-replicative virus hybrid offers the following advantages: Abundant production of potent non-infectious viral antigen (in this case Rubella) to be used as a vaccine or as a diagnostic reagent.

Other potential candidates for combinations to produce a variety of virus hybrids, for subsequent vaccine production, include Rubella virus, poliovirus, bluetongue virus, hepatitis B, HIV, etc. Some of these viruses will be briefly outlined below. This brief list is not meant to be inclusive nor limiting.

Sindbis Virus

Sindbis virus (SV) is a small RNA virus (about 12 kb) that belongs to the Alphavirus genus within the Togaviridae family. The nucleocapsid containing the single stranded viral RNA complexed with a basic capsid protein (C) is surrounded by a lipid bilayer containing two integral viral envelope spike glycoproteins designated E1 and E2. The translation of these structural proteins is initiated at a single site on a subgenomic 26S messenger RNA. The features of this virus are comprehensively studied at the molecular level (Schlesinger and Schlesinger, 1986) and was therefore chosen to serve as an example.

Rubella Virus

Rubella virus (RV), a major human pathogen, is the single member of the Rubivirus genus within the Togaviridae family (Porterfield et al, 1978 reference from Rubella paper). The virion contains three structural proteins E1, E2 and C. The capsid protein (C) is associated with the single stranded 40S genomic RNA. The E1 and E2 envelope glycoproteins form the viral spikes.

A cloned cDNA encoding the RV envelope glycoproteins E1 and E2 was used to study the ability of infected Spodoptera frugiperda (Sf9) cells to synthesize and process these glycoproteins. Oker-Blom et al (Virology, 172:82-91, 1989) demonstrated that Sf9 cells infected with the recombinant baculovirus synthesize polypeptides of the size and the antigenicity similar to those isolated from RV particles grown in VERO cells. These results clearly indicate that the BEVS is a good candidate vector for the abundant expression of recombinant RV structural glycoproteins.

Poliovirus

Urakawa et al (1989) demonstrated the synthesis of immunogenic, but non-infectious, poliovirus (PV) particles in insect cells by employing a baculovirus expression vector driven by the polyhedrin gene promoter. As demonstrated by use of the appropriate antibodies, infected insect cells made poliovirus proteins that included the structural proteins VP0, VP1 and VP3. These data suggested that processing of the poliovirus gene product by the AcLeon construct was catalyzed by the poliovirus-encoded proteases. These data demonstrate that antigenic and immunogenic poliovirus proteins and empty particles can be made in insect cells by recombinant baculoviruses.

Bluetongue Virus

Bluetongue virus is a prototype virus of the Orbivirus genus (Reoviridae family). The virus contains a genome consisting of 10 double-stranded RNA molecules (segments) each of which is unique and is believed to code for a single polypeptide product. Bluetongue virus proteins have been produced in an Sf9-baculovirus expression system. DNA sequences corresponding to the gene that codes for the bluetongue virus neutralization antigen VP2 and for the group-specific antigen VP3 have been inserted (under the transcriptional regulation of the polyhedrin gene promoter) into a baculovirus transfer vector and expressed (European Patent Application #0279661, Bishop and Roy).

Hepatitis B Virus

Bishop and Kang described the expression of human hepatitis B virus antigens in insects and in cultured insect cells. Permissive insects and cells were infected with recombinant baculoviruses that have the requisite human hepatitis B virus genes inserted into the baculovirus genome under the control of the baculovirus polyhedrin gene promoter and in lieu of the initial 5' coding sequences of the viral polyhedrin protein (European Application #0260090).

EXAMPLE 10

Homologous Recombination of a Non-Replicative Sindbis Virus into the 13.0 Map Unit Nonessential Region of Wild Type Baculovirus FIG. 11 depicts one of the many different kinds of virus or vaccines that can be produced with this specifically designed vector.

The Sindbis virus genomic RNA may be mutated, truncated or both, all in a manner that makes it non-replicative. However, the regions in the RNA that are important for encapsidation must remain intact. Oker-Blom and Summers (Journal of Virology, 63:3, 1256-1264, (1988)) used cloned cDNA for Sindbis virus 26S, encoding the structural proteins of the virus, to study protein processing of the Sindbis virus polyprotein in Sf9 cells. The transcription of the 26S mRNA, which normally occurs in the cytoplasm of Sindbis virus infected vertebrate cells, takes place in the nucleus of baculovirus infected invertebrate cells. The authors demonstrated that Sf9 cells infected with a recombinant baculovirus synthesize polypeptides that are similar to those synthesized in Sindbis virus infected BHK cells. The results thus show that Sindbis virus structural proteins that normally are encoded by non-nuclear RNAs are expressed and proteolytically processed similarly, if not identically, in Sf9 cells and BHK cells.

Homologous Recombination of a Non-Replicative Sindbis Virus into the 13.0 Map Unit Nonessential Region of Wild Type Baculovirus FIG. 11 diagrams the homologous recombination of a non-replicative Sindbis virus into the 13.0 map unit nonessential region of wild type baculovirus. Truncated genomic non-structural Sindbis virus cDNA and 26S are used as an example only. This is achieved by cloning a mutant (truncated) non-structural Sindbis virus gene under the control of an IE1 early baculovirus promoter (into the unique Bgl-II site adjacent and in the proper orientation to the IE1 promoter). The completed bacterial transfer vector is generated in a two-step fashion. First the truncated Sindbis virus non-structural gene is inserted under the control of an early baculovirus promoter (for example, IE1; FIG. 11). The next step involves inserting genes encoding intact structural Sindbis viral 26S proteins under the transcriptional regulation of a late baculovirus gene promoter (for example, polyhedrin). This insertion is performed on the recombinant baculovirus which already contains non-structural genes under the regulation of an early baculovirus gene promoter.

Mutant Sindbis viral non-structural genome is inserted 3' and therefore under the control of the IE1 early baculovirus promoter. The non-structural Sindbis viral genome must first be truncated, mutated or both prior to replacing the B-galactosidase gene. Truncation or mutation is achieved with standard methodology known to those skilled in the art. This is done in a way that makes the non-structural protein products inactive, thus, prohibiting replication of Sindbis genomic RNA by means of self replication (the non-structural proteins are responsible for replication of genomic Sindbis virus 49S RNA).

This new transfer vector is then used for transfection into Lepidopteran insect Sf9 cells together with wild type baculovirus DNA. Homologous recombination occurs at the non-essential 13.0 map unit region of the AcMPNV genome. Isolation, purification, and propagation of the extracellular recombinant baculovirus, containing the truncated non-structural Sindbis virus genes under the control of the early IE1 baculovirus promoter and Sindbis virus 26S structural gene under the control of the polyhedrin promoter, is achieved by employing standard protocols known to those skilled in the art.

These constructs are then be selected by employing the pVL1392/1393 vector which allows for insertion by homologous recombination into the Eco-RI-I fragment. The desired constructs are then verified by Southern hybridization with an appropriate piece of DNA.

During the baculovirus infection, because of the temporal transcriptional regulation of the genes, the mutated or truncated non-replicative genomic RNA of the Sindbis virus, which is under the control of an early baculovirus gene promoter, is therefore synthesized before the structural proteins, which are under the control of the late polyhedrin gene promoter. The capsid (C) protein, is expressed from the 26S cDNA and able to form nucleocapsids together with the truncated genomic RNA. The nucleocapsids become enveloped at the plasma membrane by the process of budding (a natural result of Sindbis virus infection). The budded particles can be found in the extracellular space of the recombinant baculovirus infected Sf9 cells and can be purified by conventional methods known to those skilled in the art.

While the compositions and methods of this invention have been described in terms of preferred embodiments, it will be apparent to those of skill in the art that variations and modifications may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. The method outlined in the Examples presented supra describe constructing a genetically engineered recombinant baculovirus capable of expression and assembly of non-replicative Sindbis virus particles in Sf9 cells. Sindbis virus serves only as an example. Thus, this invention allows for potential abundant production of human, animal or plant pathogens that can not replicate but which do posses a morphology (molecular structure) and immunogenicity similar or identical to their authentic counterparts. All such similar substitutes and modifications apparent to those skilled in the art are deemed to be within the spirit, scope and concept of this invention as defined by the appended claims.

We claim:

1. A recombinant baculovirus expression vector comprising an AcNPV baculovirus genome with the following components inserted into a nonessential region of the EcoRI-A fragment of wild type AcNPV baculovirus:
    a) a first DNA region consisting essentially of an AcNPV baculovirus early gene promoter;
    b) a second DNA region encoding a desired protein or portion thereof and operably linked to the early gene promoter;
    c) a third DNA region consisting essentially of an AcNPV baculovirus late gene promoter; and
    d) a fourth DNA region encoding a desired protein or portion thereof, and operably linked to the late gene promoter.

2. The recombinant baculovirus expression vector of claim 1 wherein the early baculovirus gene promoter is the promoter from the IE1 gene.

3. The recombinant baculovirus expression vector of claim 1 wherein the early baculovirus gene promoter is the promoter from the IEN gene.

4. The recombinant baculovirus expression vector of claim 1 wherein the late baculovirus gene promoter is the promoter from the polyhedrin gene.

5. The recombinant baculovirus expression vector of claim 1 wherein the late baculovirus gene promoter is the promoter from the p10 protein.

6. The recombinant baculovirus expression vector of claim 1 wherein the second DNA region encodes a non-structural viral gene and the fourth DNA region encodes a structural viral gene.

7. The recombinant baculovirus expression vector of claim 6 wherein the non-structural viral gene is mutated, truncated or both.

8. The recombinant baculovirus expression vector of claim 6 wherein the non-structural and structural viral genes include a unique signal, in an appropriate position, for initiation of transcription and for halting transcription.

9. The recombinant baculovirus expression vector of claim 6 wherein the non-structural and structural viral genes are derived from the same viral source.

10. The recombinant baculovirus expression vector of claim 6 wherein the non-structural and structural viral genes are derived from different viral sources.

11. The recombinant baculovirus of claim 1 produced in a Lepidopteran insect cell line.

12. The recombinant baculovirus of claim 11 wherein the Lepidopteran insect is selected from a group consisting of *Spodoptera frugiperda, Triohoplusia ni, Heliothis virescens, Heliothis zea, Mamestra brassicae,* or *Estigmene acrea.*

13. A recombinant transfer vector comprising a bacterial plasmid and a nonessential region of the EcoRI-A fragment of wild type AcNPV baculovirus, wherein the following components have been inserted into said nonessential region:

a) a first DNA region consisting essentially of an AcNPV baculovirus early gene promoter;

b) a second DNA region encoding a desired protein or portion thereof and operably linked to the early gene promoter;

c) a third DNA region consisting essentially of an AcNPV late gene promoter; and d) a fourth DNA region encoding a desired protein or portion thereof, and operably linked to the late gene promoter, and wherein said nonessential region is of sufficient size to promote recombination between the transfer vector and the wild-type AcNPV baculovirus.

* * * * *

UNITED STATES PATENT AND TRADEMARK OFFICE
CERTIFICATE OF CORRECTION

PATENT NO. : 5,169,784

DATED : December 8, 1992

INVENTOR(S) : MAX D. SUMMERS, CHRISTIAN E.G. OKER-BLOM

It is certified that error appears in the above-identified patent and that said Letters Patent is hereby corrected as shown below:

In the last sentence of the Abstract, delete "constructure" and replace with --construction--.

Column 11, line 19 delete "HYBRID".

Column 19, line 49 delete "pNAS" and replace with --PNAS--.

Column 24, line 40 delete "HYBRID".

Column 24, line 48 delete "HYBRID".

Signed and Sealed this

Seventh Day of December, 1993

*Attest:*

BRUCE LEHMAN

*Attesting Officer*     *Commissioner of Patents and Trademarks*